United States Patent
Nakajima et al.

(10) Patent No.: US 11,717,226 B2
(45) Date of Patent: Aug. 8, 2023

(54) BIOINFORMATION ACQUIRING APPARATUS, BIOINFORMATION ACQUIRING METHOD, AND NON-TRANSITORY RECORDING MEDIUM

(71) Applicant: CASIO COMPUTER CO., LTD., Tokyo (JP)

(72) Inventors: Mitsuyasu Nakajima, Mizuho-machi (JP); Kouichi Nakagome, Tokorozawa (JP); Takashi Yamaya, Fussa (JP); Yasushi Maeno, Ome (JP); Akira Hamada, Sagamihara (JP); Shinichi Matsui, Hamura (JP)

(73) Assignee: CASIO COMPUTER CO., LTD., Tokyo (JP)

( * ) Notice: Subject to any disclaimer, the term of this patent is extended or adjusted under 35 U.S.C. 154(b) by 198 days.

(21) Appl. No.: 17/029,786

(22) Filed: Sep. 23, 2020

(65) Prior Publication Data
US 2021/0085253 A1    Mar. 25, 2021

(30) Foreign Application Priority Data

Sep. 24, 2019    (JP) ................................ 2019-172840

(51) Int. Cl.
*A61B 5/00*    (2006.01)
*A61B 5/024*    (2006.01)
(Continued)

(52) U.S. Cl.
CPC ............ *A61B 5/7203* (2013.01); *A61B 5/024* (2013.01); *A61B 5/1102* (2013.01);
(Continued)

(58) Field of Classification Search
CPC ...... A61B 5/7203; A61B 5/024; G16H 40/67; G16H 50/30
(Continued)

(56) References Cited

U.S. PATENT DOCUMENTS 5,913,308 A *   6/1999   Forbes ..................... A61B 5/08
                                                    600/513
6,795,732 B2 *  9/2004   Stadler ............... A61N 1/36528
                                                    607/18
(Continued)

FOREIGN PATENT DOCUMENTS

JP         2018-161432 A    10/2018

*Primary Examiner* — John R Downey
(74) *Attorney, Agent, or Firm* — Scully, Scott, Murphy & Presser, P.C.

(57) ABSTRACT

A bioinformation acquiring apparatus includes at least one processor; and a memory configured to store a program to be executed in the processor. The processor acquires bioinformation in a chronological order; derives outlier level parameters, the outlier level parameter indicating a level of inclusion of outliers of the bioinformation in pieces of bioinformation acquired within a first duration; derives correction terms based on the bioinformation after removal of the outliers of the bioinformation from pieces of bioinformation acquired within a second duration that is longer than the first duration; selects one or both of a first correction procedure and a second correction procedure based on the outlier level parameters, as a correction procedure, the first correction procedure using the correction terms, the second correction procedure involving interpolation irrelevant to the correction terms; and corrects the outliers of the bioinformation within the first duration by the selected correction procedure.

7 Claims, 17 Drawing Sheets

(51) Int. Cl.
    *G16H 50/30*     (2018.01)
    *G16H 40/67*     (2018.01)
    *A61B 5/11*     (2006.01)

(52) U.S. Cl.
    CPC ........... *A61B 5/6892* (2013.01); *G16H 40/67* (2018.01); *G16H 50/30* (2018.01)

(58) Field of Classification Search
    USPC ................................ 600/300, 301, 508–528
    See application file for complete search history.

(56) References Cited

U.S. PATENT DOCUMENTS

| | | | |
|---|---|---|---|
| 8,019,410 B1* | 9/2011 | Bharmi | A61B 5/0205 600/365 |
| 2016/0029968 A1* | 2/2016 | Lerner | A61B 5/02422 600/595 |
| 2017/0154165 A1* | 6/2017 | Dempfle | A61B 5/746 |
| 2017/0231521 A1* | 8/2017 | Axelrod | A61B 5/6833 600/546 |
| 2018/0168490 A1* | 6/2018 | Jones | A61B 5/073 |
| 2019/0110751 A1* | 4/2019 | Lee | A61B 5/02055 |

\* cited by examiner

BIOINFORMATION ACQUIRING APPARATUS, BIOINFORMATION ACQUIRING METHOD, AND NON-TRANSITORY RECORDING MEDIUM

CROSS-REFERENCE TO RELATED APPLICATION

This application claims the benefit of Japanese Patent Application No. 2019-172840, filed on Sep. 24, 2019, the entire disclosure of which is incorporated by reference herein.

FIELD

This application relates to a bioinformation acquiring apparatus, a bioinformation acquiring method, and a non-transitory recording medium.

BACKGROUND

Various systems have been developed that acquire bioinformation, such as heartbeat intervals (R-R intervals: RRI), and thus determine the health state or sleep state. If any error occurs in heartbeat detection for acquiring heartbeat intervals, the acquired heartbeat intervals contain a heartbeat interval having an abnormal value, called an outlier. Some systems having a function of removing outliers have also been developed. For example, Unexamined Japanese Patent Application Publication No. 2018-161432 discloses a non-REM-sleep detection system that removes outliers from heartbeat intervals in the chronological order and compensates for defects through step interpolation. In the step interpolation, a defect is corrected using data (value closest to the defect) adjacent to the defect.

SUMMARY

A bioinformation acquiring apparatus of this application includes at least one processor; and a memory configured to store a program to be executed in the processor. The processor acquires bioinformation in a chronological order; derives outlier level parameters, the outlier level parameter indicating a level of inclusion of outliers of the bioinformation in pieces of bioinformation acquired within a first duration; derives correction terms based on the bioinformation after removal of the outliers of the bioinformation from pieces of bioinformation acquired within a second duration that is longer than the first duration; selects one or both of a first correction procedure and a second correction procedure based on the outlier level parameters, as a correction procedure, the first correction procedure using the correction terms, the second correction procedure involving interpolation irrelevant to the correction terms; and corrects the outliers of the bioinformation within the first duration by the selected correction procedure.

BRIEF DESCRIPTION OF THE DRAWINGS

A more complete understanding of this application can be obtained when the following detailed description is considered in conjunction with the following drawings, in which.

DETAILED DESCRIPTION

Embodiments of the disclosure will now be described with reference to the accompanying drawings. In these drawings, components identical to or corresponding to each other are provided with the same reference symbol.

Embodiment 1

Figure 1:
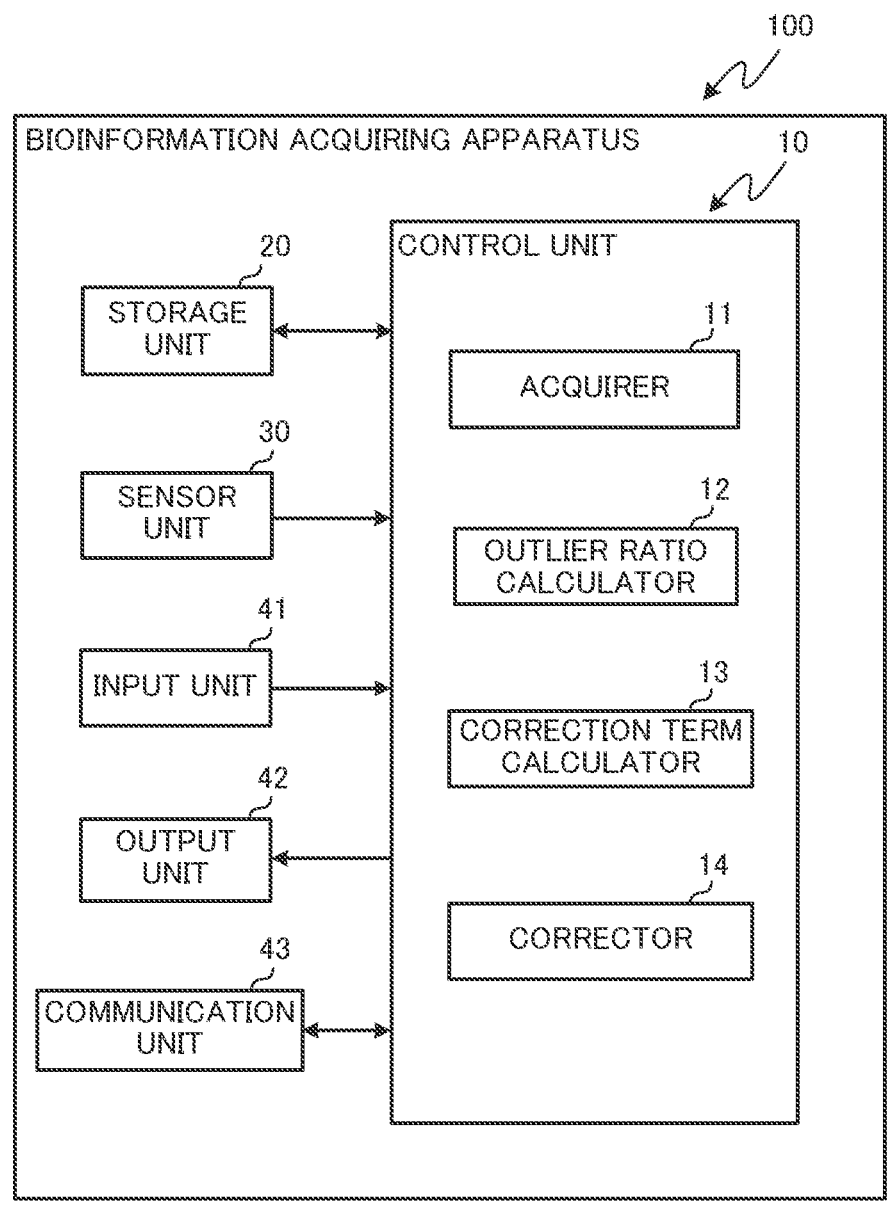
FIG. 1 illustrates an exemplary configuration of a bioinformation acquiring apparatus according to Embodiment 1.

A bioinformation acquiring apparatus 100 according to Embodiment 1 acquires heartbeat intervals of a human subject as bioinformation from a ballistocardiogram (BCG) waveform. The acquired heartbeat intervals do not have a uniform time length because of fluctuations in heartbeats, and these original heartbeat intervals therefore cannot be readily applied to analysis or other process. The bioinformation acquiring apparatus 100 thus conducts interpolation to the acquired data array of heartbeat intervals and resamples the heartbeat intervals having a uniform time length, thereby acquiring uniform heartbeat intervals (uniform RRIs). With reference to FIG. 1, the bioinformation acquiring apparatus 100 has a functional configuration including a control unit 10, a storage unit 20, a sensor unit 30, an input unit 41, an output unit 42, and a communication unit 43.

The control unit 10 includes at least one processor, such as a central processing unit (CPU). The control unit 10 executes programs stored in the storage unit 20 and thereby achieves functions of the individual components (an acquirer 11, an outlier ratio calculator 12, a correction term calculator 13, and a corrector 14), which will be described later. The control unit 10 also has a clocking function (not shown) using a timer (or clock) included in the CPU.

The storage unit 20 includes memories, such as a read only memory (ROM) and a random access memory (RAM). The ROM preliminarily stores the programs to be executed by the CPU of the control unit 10 and data necessary for execution of the programs. The RAM stores data, which is generated or altered during execution of the programs.

Figure 2:
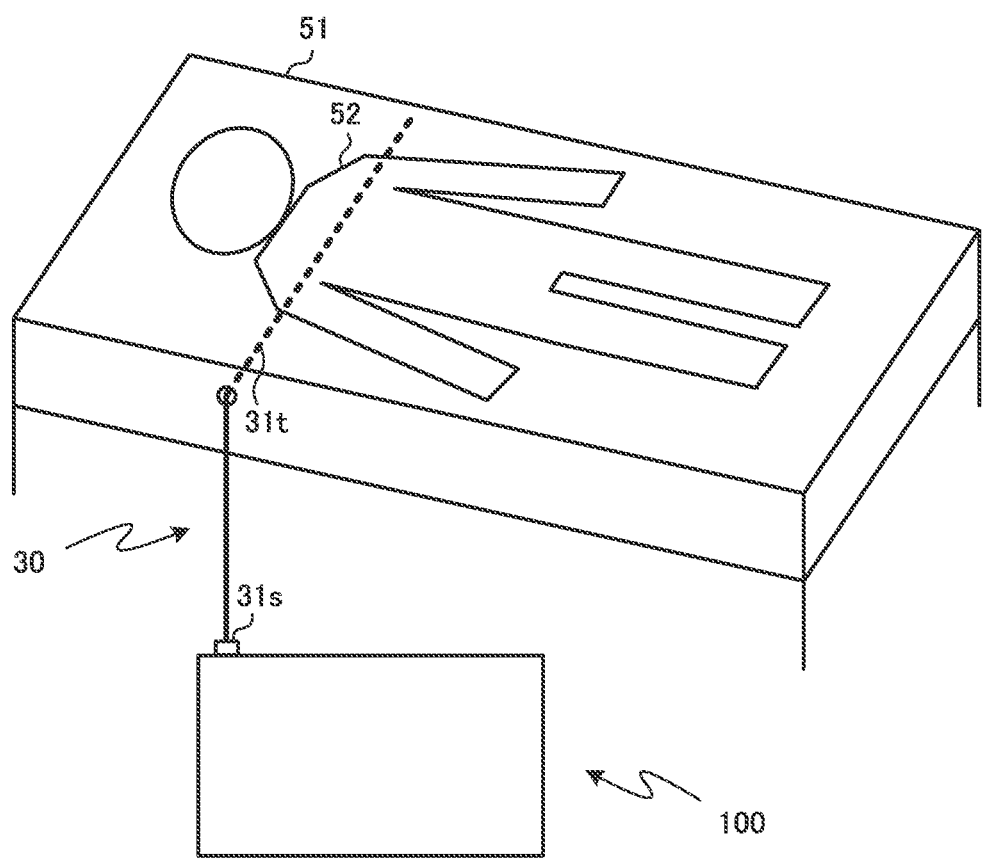
FIG. 2 illustrates a positional relationship between a lying human subject and a tube included in a sensor unit.

The sensor unit 30 includes a sensor for detecting body vibrations, and thus detects biosignals (ballistocardiogram signals in the embodiment) for acquiring bioinformation (heartbeat intervals in the embodiment) from a certain portion of a target (human subject in the embodiment). Specifically, as illustrated in FIG. 2, the sensor unit 30 is equipped with a tube 31$t$ extending under a mattress 51 on which the target lies, and a sensor 31$s$ for detecting an air pressure in the tube 31$t$. While the target is lying on the mattress 51, the sensor 31$s$ detects the air pressure in the tube and can thus acquire the detected air pressure as ballistocardiogram signals representing the ballistocardiogram waveform of the target. The ballistocardiogram signals can be acquired because the air pressure detected by the sensor 31$s$ varies depending on body vibrations of the target resulting from heartbeats of the target. The tube may also extend on or inside the mattress 51, instead of under the mattress 51.

In order to acquire ballistocardiogram signals, movements of the body around the scapulae of a human subject 52 should be captured in general. The tube 31$t$ is therefore disposed at a position corresponding to the vicinity of the scapulae of the human subject 52 lying on the mattress 51. The configuration illustrated in FIG. 2 includes only one tube but may include two or more tubes (in the case of two or more tubes, the configuration further includes sensors corresponding to the respective tubes). The component for capturing body vibrations of the human subject 52 resulting from heartbeats should not necessarily be a tube and may be a piezoelectric element disposed under the matless, which serves as a sensor included in the sensor unit 30 in place of the tube. The sensor unit 30 should not necessarily be provided to a mattress and may be installed in a chair, for example. In an exemplary case of the sensor unit 30 installed in the chair, the bioinformation acquiring apparatus 100 is able to acquire ballistocardiogram signals of the human subject 52 sitting on the chair.

The input unit 41 includes, for example, a keyboard, a mouse, or a touch panel. The input unit 41 is an interface for receiving a user operation. A typical example of the user operation is an instruction to start or end the acquisition of heartbeat intervals.

The output unit 42 includes, for example, a liquid crystal display (LCD) or an electroluminescence (EL) display. The output unit 42 displays heartbeat intervals acquired by the bioinformation acquiring apparatus 100, for example.

The communication unit 43 is a communication interface for transmitting and receiving data and the like to and from other external devices. The communication interface may perform wireless or wired communication. The bioinformation acquiring apparatus 100 is able to transmit the acquired heartbeat intervals, for example, to an external server via the communication unit 43.

The functional configuration of the control unit 10 of the bioinformation acquiring apparatus 100 will now be described. The control unit 10 achieves the functions of the acquirer 11, the outlier ratio calculator 12, the correction term calculator 13, and the corrector 14, so as to acquire and correct heartbeat intervals.

Based on the value (air pressure) detected by the sensor included in the sensor unit 30 and the time of detection, the acquirer 11 acquires the air pressure as ballistocardiogram signals, and acquires a data array of beat-to-beat intervals (BBIs) corresponding to heartbeat intervals in the chronological order from the acquired ballistocardiogram signals. In more detail, the acquirer 11 samples the ballistocardiogram signals output from the sensor of the sensor unit 30 at a certain sampling frequency (for example, 100 Hz), acquires a data array 200 of the ballistocardiogram signals illustrated in FIG. 3, and then acquires a data array of BBIs from the data array 200 of ballistocardiogram signals. The sampling frequency should not necessarily be 100 Hz and may be any frequency provided that the ballistocardiogram signals can be acquired. A typical sampling frequency is approximately 80 to 100 Hz.

The data array of BBIs may be acquired from the data array 200 of ballistocardiogram signals in any procedure. An exemplary procedure (explained later) involves extracting heartbeat timings through detection of local maximum amplitudes (detection of peak values) from the data array 200 of ballistocardiogram signals using a window having a certain duration (for example, 1.2 seconds), and acquiring, as a BBI, each time interval between two heartbeat timings temporally adjacent to each other. The heartbeat timing indicates a timing of occurrence of a heartbeat. In this embodiment, the time interval between two heartbeat timings temporally adjacent to each other is estimated to be a BBI corresponding to the heartbeat interval. The heartbeat timing can be estimated using the timer (or clock) included in the CPU and the data array of ballistocardiogram signals as explained above, and may also be estimated by other appropriate procedure, such as sampling of pulse waves. The BBI is the acronym of a beat-to-beat interval, which indicates a time interval between a beat and the subsequent beat.

Figure 3:
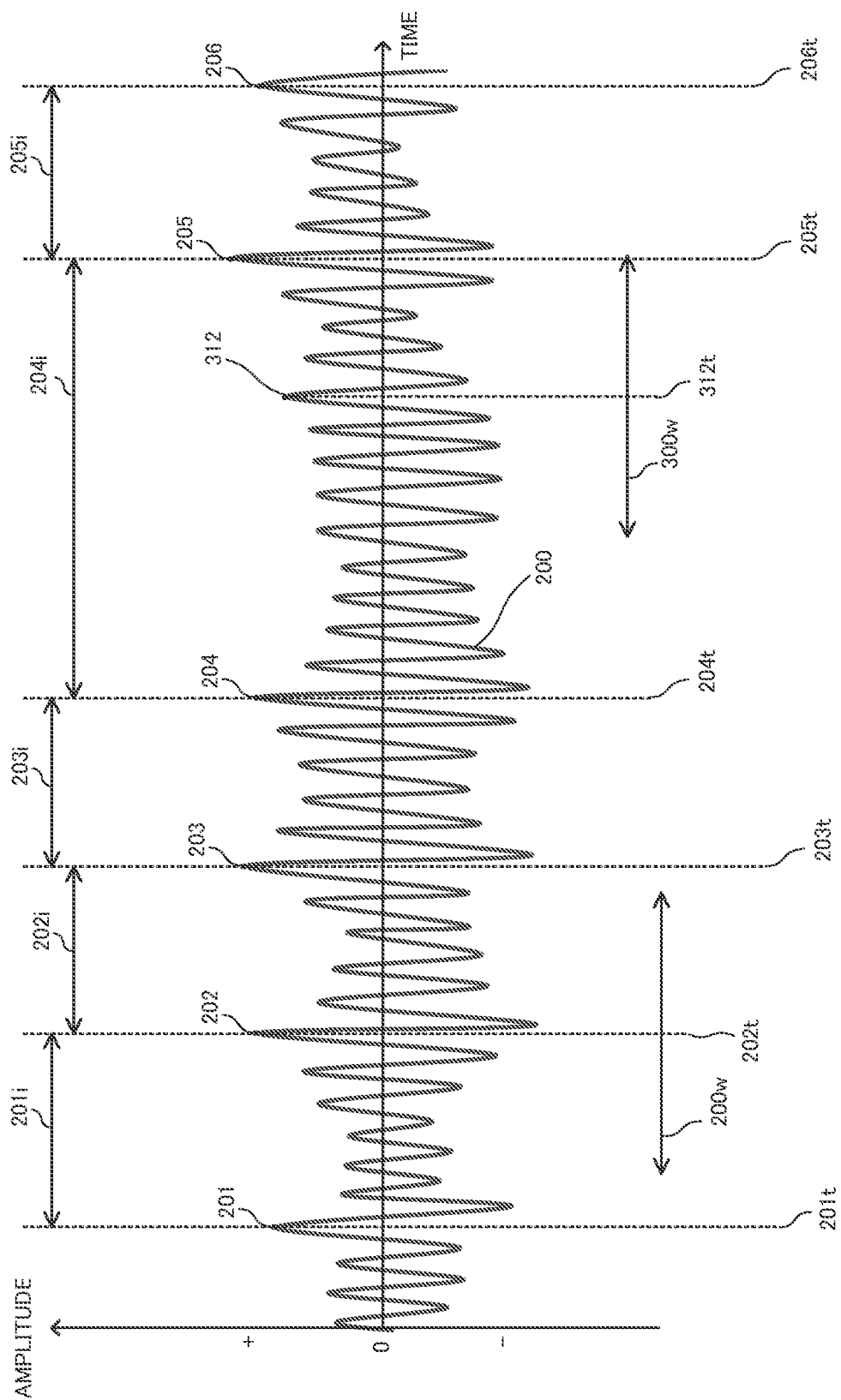
FIG. 3 illustrates an exemplary data array of ballistocardiogram signals.

The procedure of acquiring the data array of BBIs will now be explained in more detail. For example, the acquirer 11 detects the peak value (local maximum amplitude) within a time window 200$w$ having a focused timing at the center from the data array 200 of ballistocardiogram signals illustrated in FIG. 3, while shifting the focused timing along the time axis. The time window 200$w$ has a fixed duration (for example, 1.2 seconds) slightly shorter than the double of a heartbeat interval. If the timing of the detected peak value accords with the focused timing, the acquirer 11 extracts this focused timing as a heartbeat timing. In FIG. 3, if attention is focused on a point 202 representing a sampled ballistocardiogram signal, since the peak value of the ballistocardiogram signals within the time window 200$w$ is represented by the point 202, the timing of occurrence of a ballistocardiogram signal represented by the point 202 is extracted as a heartbeat timing 202$t$. In contrast, for example, if attention is focused on a point 312, the peak value of the ballistocardiogram signal within a time window 300$w$ having the same duration is represented by not the point 312 but a point 205. The timing 312$t$ of occurrence of a ballistocardiogram signal represented by the point 312 is therefore not extracted as a heartbeat timing.

Figure 4:
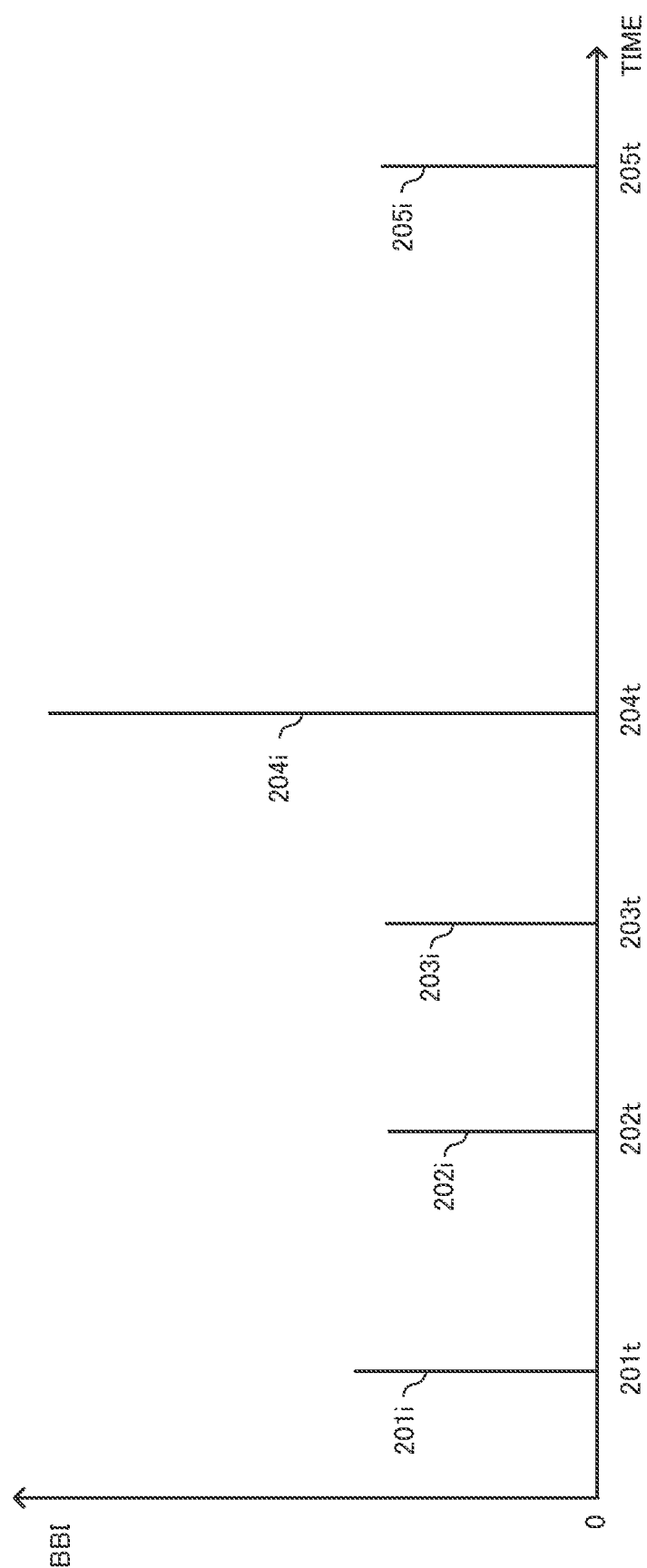
FIG. 4 illustrates exemplary acquired BBIs.

In this manner, the acquirer 11 extracts heartbeat timings 201$t$, 202$t$, 203$t$, 204$t$, 205$t$, and 206$t$, and then acquires, as BBIs, time intervals 201$i$, 202$i$, 203$i$, 204$i$, and 205$i$ between every two heartbeat timings temporally adjacent to each other among the extracted heartbeat timings. FIG. 4 is a graph obtained by plotting the data array of BBIs acquired by the acquirer 11, with the BBI on the y axis and the time on the x axis.

The outlier ratio calculator 12 calculates an outlier ratio, which indicates the level of inclusion of BBI outliers in the BBIs (data array of BBIs) acquired by the acquirer 11 during a first duration (for example, one minute). The outlier ratio is also called an outlier level parameter.

The BBI outlier indicates an unexpected value as a heartbeat interval of a human. For example, no human has a heartbeat interval of two seconds or more. A BBI of two seconds or more is therefore estimated to be an outlier among the data array of BBIs. In this embodiment, the estimation of BBI outliers is achieved by an outlier estimation (explained later). For example, a BBI represented by the time interval 204*i* in FIG. 4 is estimated to be a BBI outlier by the outlier estimation (explained later).

In the calculation of each outlier ratio according to the embodiment, the outlier ratio calculator 12 calculates an outlier ratio (outlier level parameter), which is a ratio of BBIs estimated to be outliers to all the BBIs acquired during the first duration including the focused timing (for example, the one minute having the focused timing at the center), while shifting the focused timing along the time axis. That is, the outlier ratio can be obtained from the total number of BBIs and the number of outliers within the first duration, using the expression (1) below:

Outlier ratio=the number of BBI outliers within the first duration÷the total number of BBIs within the first duration   (1)

In an exemplary case where the first duration is one minute having the focused timing at the center and no outlier is included in the BBIs during the one minute, the outlier ratio at this focused timing is 0. In another exemplary case where outliers occupy the half of the BBIs during the one minute, the outlier ratio at this focused timing is 0.5. In another exemplary case where all the BBIs are outliers, the outlier ratio at this focused timing is 1.

Figure 5:
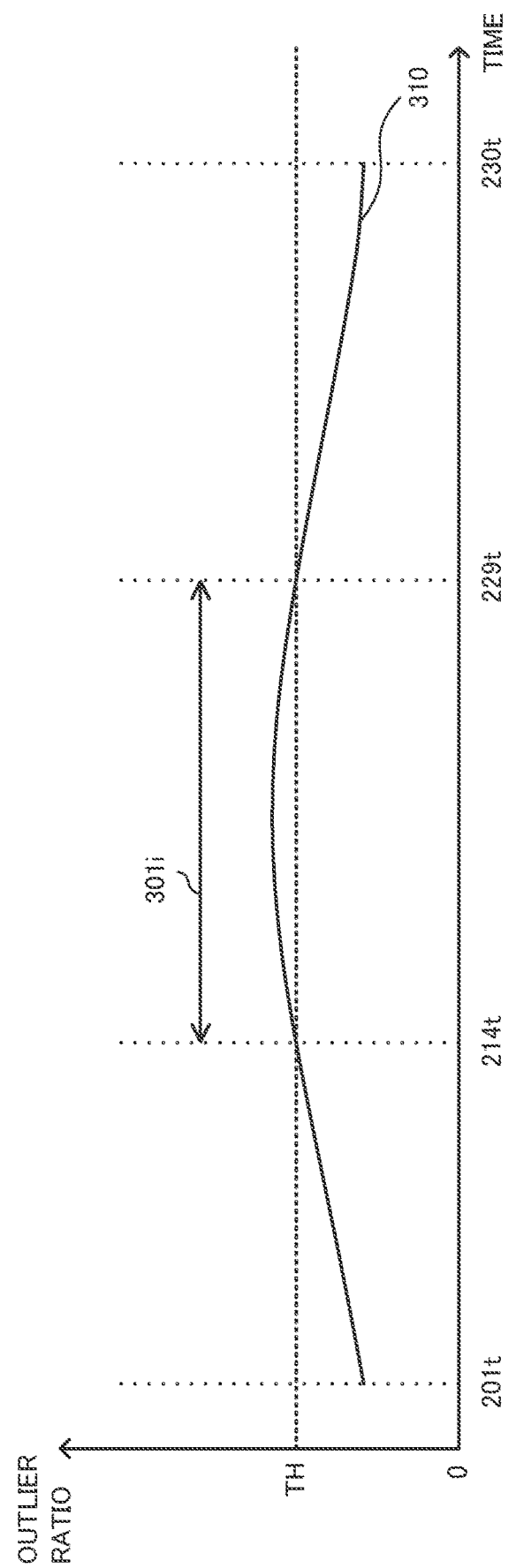
FIG. 5 illustrates an exemplary outlier ratio within a first duration including a focused timing, which is calculated while the focused timing is being shifted along the time axis.

The outlier ratio calculator 12 calculates a single outlier ratio every focused timing while shifting the focused timing. In an exemplary case of shifting the focused timing by one second, the outlier ratio calculator 12 calculates an outlier ratio every one second. The following description assumes that a larger number of outliers are included in the BBIs from the timings 214*t* and 229*t* among the BBIs acquired by the acquirer 11 from the timings 201*t* to 230*t* as illustrated in FIG. 5. In this case, the outlier ratio calculator 12 calculates outlier ratios for BBIs within the first duration including the focused timing while shifting the focused timing, and thus acquires a data array of outlier ratios as illustrated in FIG. 5, for example. FIG. 5 illustrates a data array 310 depicted by connecting the points representing individual outlier ratios.

The time displacement (calculation cycle of outlier ratios (outlier level parameters)) of shifting of the focused timing during the calculation of outliers in the outlier ratio calculator 12 should not necessarily be identical to the cycle of resampling interpolation in BBIs during the BBI correction (explained later). If the calculation cycle of outlier ratios is made identical to the cycle of resampling interpolation in BBIs, an outlier ratio is calculated at each timing corresponding to a resampled BBI. These cycles therefore should preferably be identical to each other in order to calculate an outlier ratio most corresponding to each BBI. In this embodiment, both of the cycle of resampling interpolation in BBIs and the calculation cycle of outlier ratios are defined to be one second.

The correction term calculator 13 calculates, as a correction term, a representative value of BBIs after removal of BBI outliers from the BBIs acquired within a time window having a second duration (for example, the five minutes having the focused timing at the center). The second duration is longer than the first duration and encompasses the first duration. The representative value of BBIs used as a correction term is the average in this embodiment. The correction term calculator 13 calculates the average of BBIs after removal of BBI outliers from the BBIs within the time window having the second duration (five minutes having the focused timing at the center), and thereby provides a correction term for BBIs within the second duration every focused timing. The correction term calculator 13 may perform derivation by using a table or the like instead of performing a calculation (derivation) by using an expression or the like. The second duration is only required to include the focused timing and does not have to have the focused timing at the center.

Figure 6:
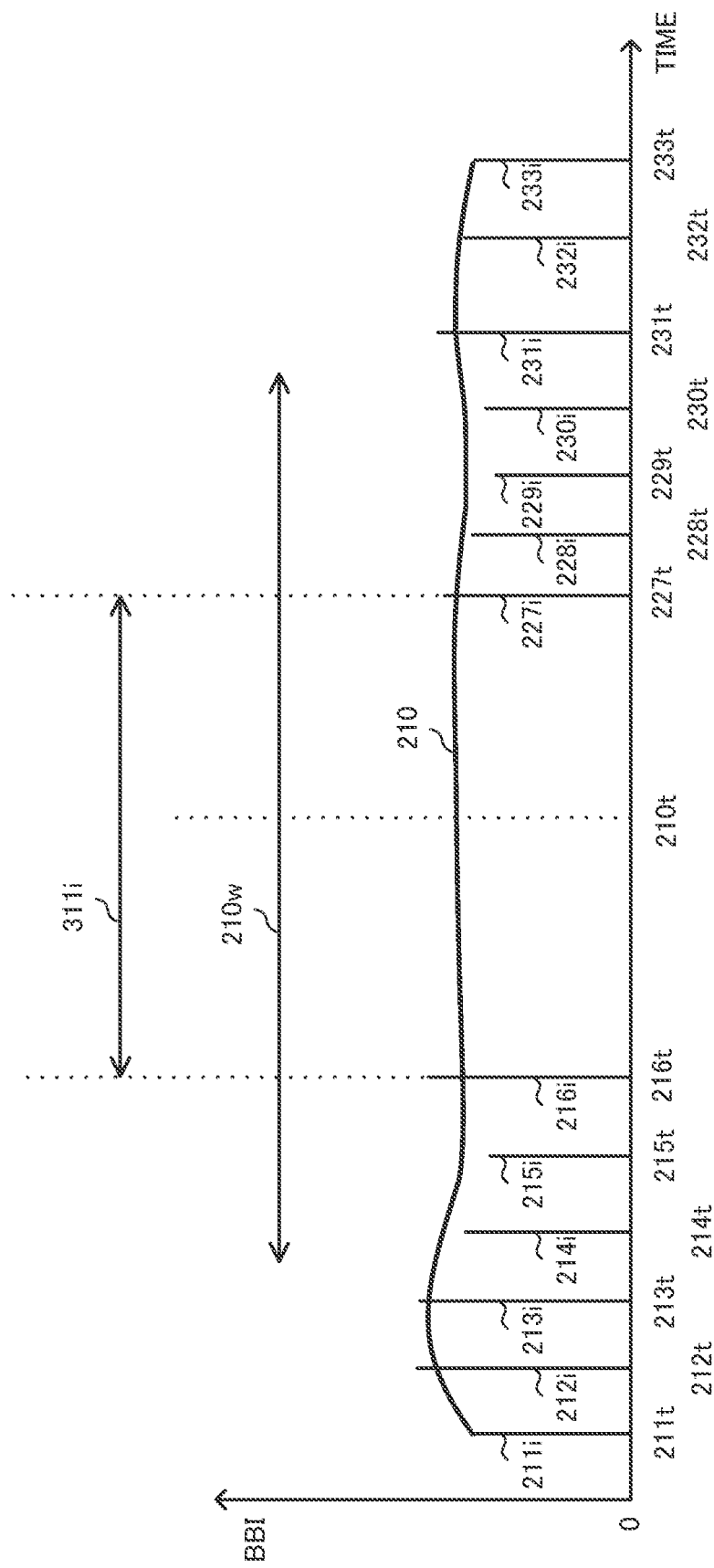
FIG. 6 illustrates an exemplary average of BBIs within a second duration including a focused timing, which is calculated while the focused timing is being shifted along the time axis.

FIG. 6 illustrates an example in which the data array of BBIs acquired by the acquirer 11 after outlier removal are BBIs 211*i*, 212*i*, . . . , and 233*i* (the BBIs 216*i* and 227*i* have a gap therebetween because of the outlier removal). In order to calculate a correction term at a focused timing 210*t*, the correction term calculator 13 calculates the average of BBIs 214*i*, 215*i*, 216*i*, 227*i*, 228*i*, 229*i*, and 230*i* within a time window 210*w* having the second duration having the timing 210*t* at the center.

The correction term calculator 13 calculates such correction terms (moving averages) while shifting the focused timing, like the outlier ratio calculator 12, and thus provides a single correction term every focused timing. The time displacement (calculation cycle of correction terms) of shifting of the focused timing may be any value. If the calculation cycle of correction terms is made identical to the cycle of resampling interpolation in BBIs, a correction term is calculated at each timing corresponding to a resampled BBI, like the calculation cycle of outlier ratios. These cycles therefore should preferably be identical to each other in order to calculate a correction term most corresponding to each BBI. In this embodiment, the time displacement (calculation cycle of correction terms) of shifting of the focused timing in the correction term calculator 13 is also defined to be one second.

The correction term calculator 13 sequentially calculates correction terms while shifting the focused timing along the time axis, and thereby acquires a data array of correction terms as illustrated in FIG. 6, for example. FIG. 6 illustrates a curve 210 depicted by connecting the points representing the individual correction terms. In FIG. 6, the BBIs acquired within a period 311*i* between timings 216*t* and 227*t* are all removed as outliers. Since the actual duration of the time window 210*w* is five minutes, for example, the number of BBIs acquired within the time window 210*w* is approximately several hundreds. FIG. 6 illustrates only some of the BBIs in order to simplify the explanation.

Based on the outlier level parameters calculated by the outlier ratio calculator 12, the corrector 14 corrects the BBI outliers within the first duration using the correction terms calculated by the correction term calculator 13. In more detail, if the outlier level parameters calculated by the outlier ratio calculator 12 are at least a certain threshold (outlier ratio threshold TH (for example, 0.5)), then the corrector 14 corrects the BBI outliers within the first duration using the correction terms calculated by the correction term calculator 13. This correction procedure using the correction terms is called a first correction procedure.

Specifically, in the case where the calculation in the outlier ratio calculator 12 provides the data array 310 of outlier ratios (outlier level parameters) as illustrated in FIG.

5, the corrector 14 corrects the BBI outliers using the correction terms (curve 210 in FIG. 6) calculated by the correction term calculator 13 within a period 301$i$ in FIG. 5, in which the outlier ratios are at least the outlier ratio threshold TH.

If the outlier ratios calculated by the outlier ratio calculator 12 are lower than the certain threshold (outlier ratio threshold TH), the corrector 14 corrects the BBI outliers by a correction procedure involving interpolation irrelevant to the correction terms calculated by the correction term calculator 13. The correction procedure involving interpolation irrelevant to correction terms indicates a correction procedure using interpolation, such as spline interpolation, cubic interpolation, linear interpolation, or piecewise cubic Hermite interpolating polynomial (PCHIP) interpolation, based on the BBIs after outlier removal from the acquired BBIs, for example. This correction procedure involving interpolation irrelevant to correction terms is called a second correction procedure.

Figure 7:
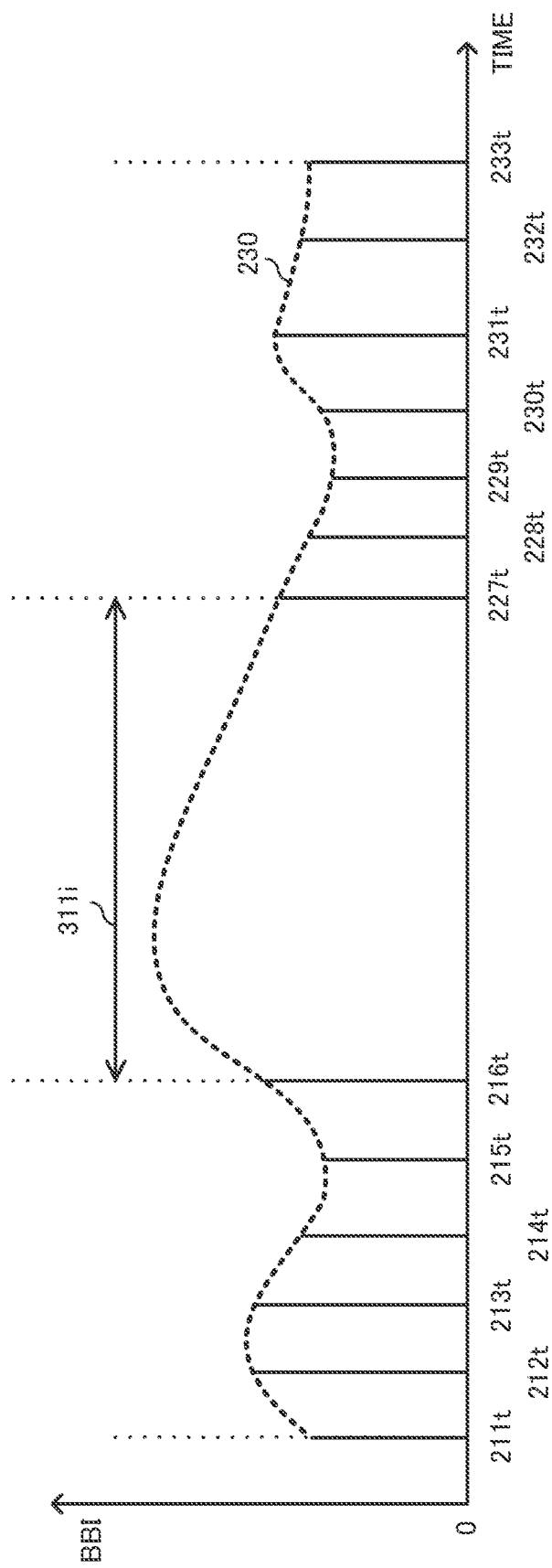
FIG. 7 illustrates exemplary BBIs after spline interpolation.
Figure 8:
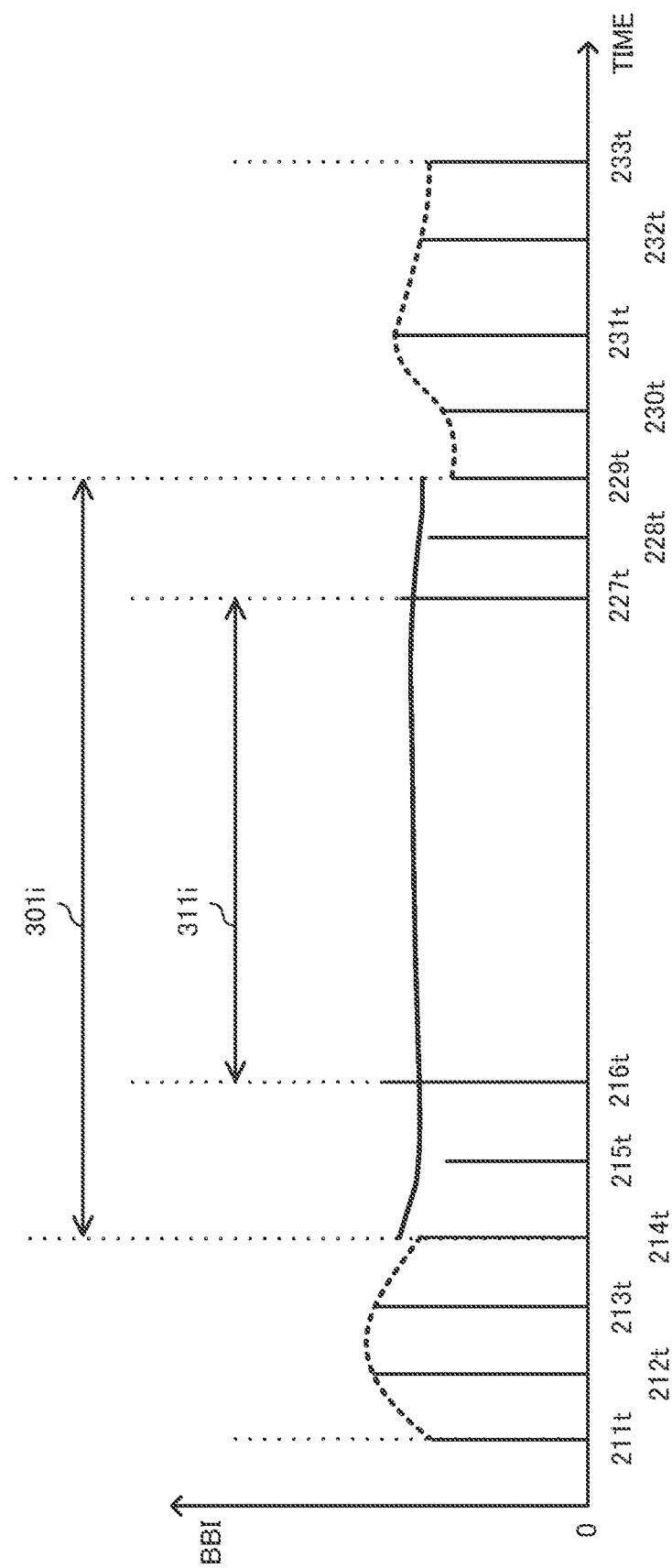
FIG. 8 illustrates an example in which BBIs are corrected by switching correction procedures between correction using correction terms and spline interpolation.

FIG. 7 illustrates a curve 230 within the period 311$i$ according to a comparative example in which spline interpolation is conducted within the period 301$i$ providing high outer ratios. As is apparent from this curve 230, the correction involving interpolation irrelevant to correction terms may interpolate values significantly deviated from the true values within the period of unsuccessful acquisition of BBIs. In order to solve this problem, the corrector 14 corrects outliers within the period 301$i$ that provides high outlier ratios (and is supposed to have high levels of outliers) by the first correction procedure using correction terms, and corrects outliers within the durations (except for the period 301$i$) that provide low outlier ratios (and are supposed have low levels of outliers) by the second correction procedure involving interpolation irrelevant to correction terms, that is, interpolation using the BBIs after removal of outliers from the acquired BBIs, as illustrated in FIG. 8.

The above description focuses on the functional configuration of the bioinformation acquiring apparatus 100. A bioinformation acquiring process of the bioinformation acquiring apparatus 100 will now be explained with reference to FIG. 9. If the bioinformation acquiring apparatus 100 receives an instruction to start the bioinformation acquiring process from a user via the input unit 41, the bioinformation acquiring apparatus 100 starts the bioinformation acquiring process. The user of the bioinformation acquiring apparatus 100 may be or may not be identical to the human subject in the bioinformation acquiring process.

The acquirer 11 of the bioinformation acquiring apparatus 100 first acquires ballistocardiogram signals detected by the sensor 31$s$ of the sensor unit 30 (Step S101). In general, Step S101 is repeated continuously during a biosignal acquisition period (for example, the period from when the human subject 52, who is the target of acquisition of heartbeat interval, goes to bed (lies on the mattress) until when the human subject 52 gets up). While the step S101 is being repeated, the acquirer 11 stores the values (ballistocardiogram signals) detected by the sensor 31$s$ of the sensor unit 30 in association with the times of detection in the chronological order into the storage unit 20. In Step S101, the acquirer 11 needs not to be informed of the exact time when the human subject goes to bed or gets up, and may operate during a biosignal acquisition period (for example, from 23 to 7 o'clock) set by a simple timer function. Alternatively, the biosignal acquisition period may be set in accordance with instructions (instructions to start and end the acquisition of ballistocardiogram signals) from the input unit 41.

The acquirer 11 then acquires a data array of BBIs in the chronological order, as explained above, based on the values (ballistocardiogram signals) detected by the sensor 31$s$ and stored in the storage unit 20, and stores the data array into the storage unit 20 (Step S102).

The outlier ratio calculator 12 then conducts an outlier estimation, which will be explained later (Step S103). Based on the outliers provided by the outlier estimation in Step S103, the outlier ratio calculator 12 calculates outlier ratios for BBIs within the first duration including the focused timing, while shifting the focused timing along the time axis by a certain time (for example, one second) (Step S104). The first duration is, for example, the one minute from the time of 30 seconds before the focused timing and the time of 30 seconds after the focused timing. The outlier ratio calculator 12 then stores all the calculated outlier ratios (data array of outlier ratios in the chronological order) into the storage unit 20.

Figure 10:
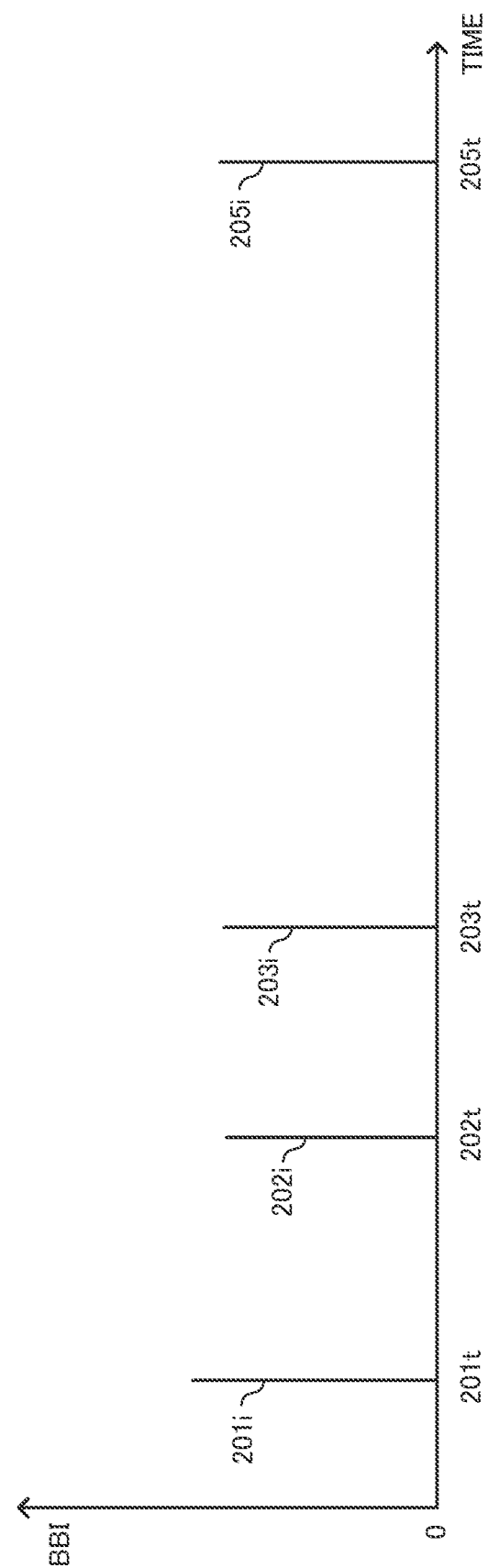
FIG. 10 illustrates exemplary BBIs after outlier removal.

The outlier ratio calculator 12 then removes outliers from the data array of BBIs in the chronological order stored in the storage unit 20 (Step S105). In an exemplary case where the acquirer 11 acquires the data array of BBIs illustrated in FIG. 4 in Step S102, the BBI represented by the time interval 204$i$ is estimated to be a BBI outlier in Step S103, and is removed in Step S105, resulting in the data array of BBIs illustrated in FIG. 10.

Based on the data array of BBIs after outlier removal, the correction term calculator 13 calculates, as correction terms, the averages of the BBIs within the second duration including the focused timing, while shifting the focused timing along the time axis by a certain time (for example, one second), and then stores the calculated correction terms into the storage unit 20 (Step S106). The second duration is, for example, the five minutes from the time of 2.5 minutes before the focused timing and the time of 2.5 minutes after the focused timing.

The corrector 14 then conducts a BBI correction, which will be explained later (Step S107). The corrector 14 outputs the corrected BBIs as heartbeat intervals to the output unit 42 (Step S108), and then terminates the bioinformation acquiring process. The corrector 14 may also transmit the corrected BBIs to an external device via the communication unit 43 in Step S108, instead of outputting the corrected BBIs to the output unit 42. Alternatively, the corrector 14 may only store the corrected BBIs into the storage unit 20 and terminate the bioinformation acquiring process.

The outlier estimation (Step S103) involved in the bioinformation acquiring process will now be explained with reference to FIG. 11.

The outlier ratio calculator 12, first, sequentially reads a BBI as a focused BBI from the data array of BBIs in the chronological order stored in the storage unit 20 in the order of storage of BBIs (Step S201). The outlier ratio calculator 12 then determines whether the focused BBI is smaller than a first threshold (TH1) (Step S202). If the focused BBI is not smaller than the first threshold (Step S202; No), the processing goes to Step S205.

If the focused BBI is smaller than the first threshold (Step S202; Yes), the outlier ratio calculator 12 determines whether an adjacent BBI difference is smaller than a second threshold (TH2) (Step S203). The adjacent BBI difference indicates the absolute value of the difference between the focused BBI and the next BBI subsequent (adjacent) to the focused BBI, and is also called an adjacent interval difference. If the adjacent BBI difference is not smaller than the second threshold (Step S203; No), the processing goes to Step S205.

If the adjacent BBI difference is smaller than the second threshold (Step S203; Yes), the outlier ratio calculator 12 determines whether a second adjacent BBI difference is smaller than a third threshold (TH3) (Step S204). The second adjacent BBI difference indicates the sum of the adjacent BBI difference (the absolute value of the difference between the focused BBI and the next BBI subsequent to the focused BBI) in Step S203 and its following adjacent BBI difference (the absolute value of the difference between the next BBI and the next-next BBI subsequent to the next BBI). If the second adjacent BBI difference is not smaller than the third threshold (Step S204; No), the processing goes to Step S205.

If the second adjacent BBI difference is smaller than the third threshold (Step S204; Yes), the processing goes to Step S206.

In Step S205, the outlier ratio calculator 12 estimates the focused BBI to be an outlier and proceeds to Step S206. In Step S205, the focused BBI stored in the storage unit 20 may be provided with flag information indicating an estimation result of an outlier, so as to clearly demonstrate that this focused BBI was estimated to be an outlier by the outlier ratio calculator 12.

In Step S206, the outlier ratio calculator 12 determines whether the data array of BBIs in the chronological order stored in the storage unit 20 contains any BBI subsequent to the focused BBI. If the data array contains any subsequent BBI (Step S206; Yes), the processing returns to Step S201. If the data array contains no subsequent BBI (Step S206; No), the outlier ratio calculator 12 terminates the outlier estimation, and then the processing returns to Step S104 of the bioinformation acquiring process.

Figure 12:
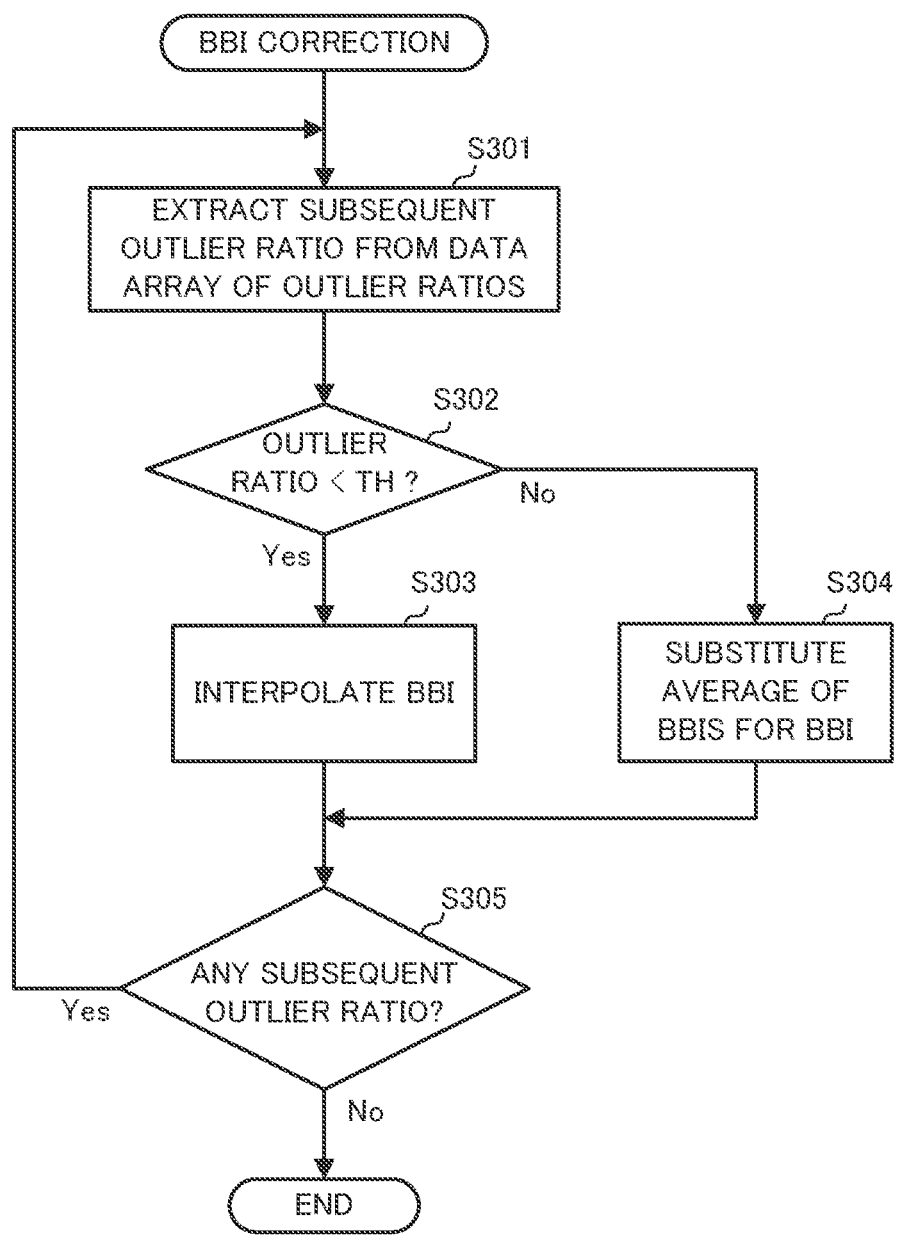
FIG. 12 is a flowchart of a BBI correction according to Embodiment 1.

The BBI correction (Step S107) involved in the bioinformation acquiring process will now be explained with reference to FIG. 12. This process involves resampling interpolation in BBIs at a resampling frequency (for example, 1 Hz). The resampling frequency may be any value as described above. In this embodiment, the resampling frequency is adjusted to 1 Hz in accordance with the one second as the calculation cycle of outlier ratios. In the case of the resampling frequency of 1 Hz, a BBI is resampled every one second. Since the outlier ratios stored in the storage unit 20 were acquired every one second as explained above, a single BBI should be resampled every time when a single outlier ratio is extracted in this embodiment. The data array of outlier ratios, data array of BBIs, and data array of correction terms are all on the same time axis. Accordingly, in the following explanation, the outlier ratio, the BBI, and the correction term at a certain focused timing (t) are respectively represented by E[t], B[t], and C[t]. Also, the data at the timing immediately after the focused timing (t) on the time axis are respectively represented by E[t+1], B[t+1], and C[t+1].

The corrector 14, first, sequentially reads an outlier ratio as a focused outlier ratio (E[t]) from the data array of outlier ratios in the chronological order stored in the storage unit 20 in the order of storage of outlier ratios (Step S301).

The corrector 14 then determines whether the focused outlier ratio (E[t]) is lower than the outlier ratio threshold TH (for example, 0.5) (Step S302).

If the focused outlier ratio is lower than the outlier ratio threshold TH (Step S302; Yes), the corrector 14 resamples the BBI (B[t]) associated with the focused timing associated with the focused outlier ratio (E[t]) by an interpolation procedure of substituting an BBI after outlier removal for the BBI (B[t]) (Step S303). This step may involve any interpolation procedure. Exemplary interpolation procedures include spline interpolation, cubic interpolation, linear interpolation, and PCHIP interpolation, as described above.

In contrast, if the focused outlier ratio (E[t]) is not lower than the outlier ratio threshold TH, (Step S302; No), the corrector 14 resamples the BBI (B[t]) associated with the focused timing associated with the focused outlier ratio (E[t]) by substituting the correction term associated with the focused timing (that is, the correction term (C[t]) calculated by the correction term calculator 13) for the BBI (B[t]) (Step S304). Alternatively, in Steps S303 and S304, the corrector 14 may correct (resample) only outliers while maintaining the BBIs except for the outliers as they are, as a BBI associated with each focused timing.

The corrector 14 then determines whether the data array of outlier ratios stored in the storage unit 20 contains any outlier ratio (E[t+1]) subsequent to the focused outlier ratio (E[t]) (Step S305). If the data array contains any subsequent outlier ratio (Step S305; Yes), the processing returns to Step S301 (in Step S301, (t) is incremented to (t+1)). If the data array contains no subsequent outlier ratio (Step S305; No), the corrector 14 terminates the BBI correction and returns to Step S108 of the bioinformation acquiring process.

The first, second, and third thresholds are preliminarily determined based on experiments, and may be varied depending on a human subject. For example, these thresholds may be set in accordance with the heart rate and the adjacent BBI difference of a human subject if these parameters are known. Alternatively, the thresholds may be varied depending on the age of a human subject, because the heart rate and the adjacent BBI difference decrease with aging in general (note that the BBI is the inverse of the heart rate).

For example, reference thresholds are preliminarily determined for all ages based on experiments (these reference thresholds based on the experiments are respectively called a first reference threshold, second reference threshold, and third reference threshold). For a human subject in a young age (a first reference age (for example, age of 20) or younger), the first threshold is decreased (for example, by dividing the first reference threshold by a young-age first factor), while the second and third thresholds are increased (for example, by multiplying the second reference threshold by a young-age second factor and multiplying the third reference threshold by a young-age third factor). It should be noted that these factors (collectively called age factors) are all larger than 1. Alternatively, only one or two of the three thresholds may be varied.

In contrast, for a human subject in an old age (a second reference age (for example, age of 60) or older), the first threshold is increased (for example, by multiplying the first reference threshold by an old-age first factor), while the second and third thresholds are decreased (for example, dividing the second reference threshold by an old-age second factor and dividing the third reference threshold by an old-age third factor). It should be noted that these age factors are all larger than 1. Alternatively, only one or two of the three thresholds may be varied.

The first threshold may also be affected by a moving state (for example, a sleeping state, sitting state, or exercising state) of a human subject. Specifically, as the degree of stillness of the human subject rises, the first threshold increases. In contrast, as the degree of hard exercise of the human subject rises, the first threshold decreases.

Accordingly, for example, the first threshold obtained based on experiments on a human subject in a sleeping state is used as the first reference threshold. Depending on the moving state of the human subject, the first threshold for a sitting state may be defined to be the value calculated by dividing the first reference threshold by a moving state factor for a sitting state (for example, 1.2), and the first threshold for an exercising state may be defined to be the value calculated by dividing the first reference threshold by a moving state factor for an exercising state (for example, 1.5). Alternatively, the thresholds may be set using both of the age factor and the moving state factor. The thresholds are thus varied depending on the age and moving state of a human subject, thereby achieving estimation of outliers with higher accuracy. It should be noted that the age and moving state of a human subject are input through the input unit 41 and are used for determination of the thresholds in the outlier ratio calculator 12.

Although the above-explained outlier estimation involves determination of three conditions including all the three thresholds, the outlier estimation is only required to involve determination of at least one condition among the three conditions and may exclude determination of the rest conditions.

The above-explained bioinformation acquiring process, outlier estimation, and BBI correction can achieve appropriate selection of a correction (resampling) procedure for BBIs depending on the outlier ratios. This configuration is capable of appropriate correction of BBIs, unlike the above-mentioned existing configuration, even in the case where outliers cannot be appropriately removed (for example, outliers cannot be completely removed, or a large number of BBIs are removed as outliers). In addition, the outlier ratio calculator 12 calculates outlier ratios while shifting the first duration along the time axis, so that the corrector 14 can select the optimum correction procedure at each timing in the case where the outlier ratios vary with time. Furthermore, the outlier ratio calculator 12 performs estimation of outliers based on the first threshold, the second threshold, and the third threshold, and can thus achieve estimation of outliers with higher accuracy. In addition, the correction term calculator 13 calculates correction terms while shifting the time window having the second duration along the time axis, and can thus achieve calculation of the optimum correction term at each timing.

Embodiment 2

Figure 13:
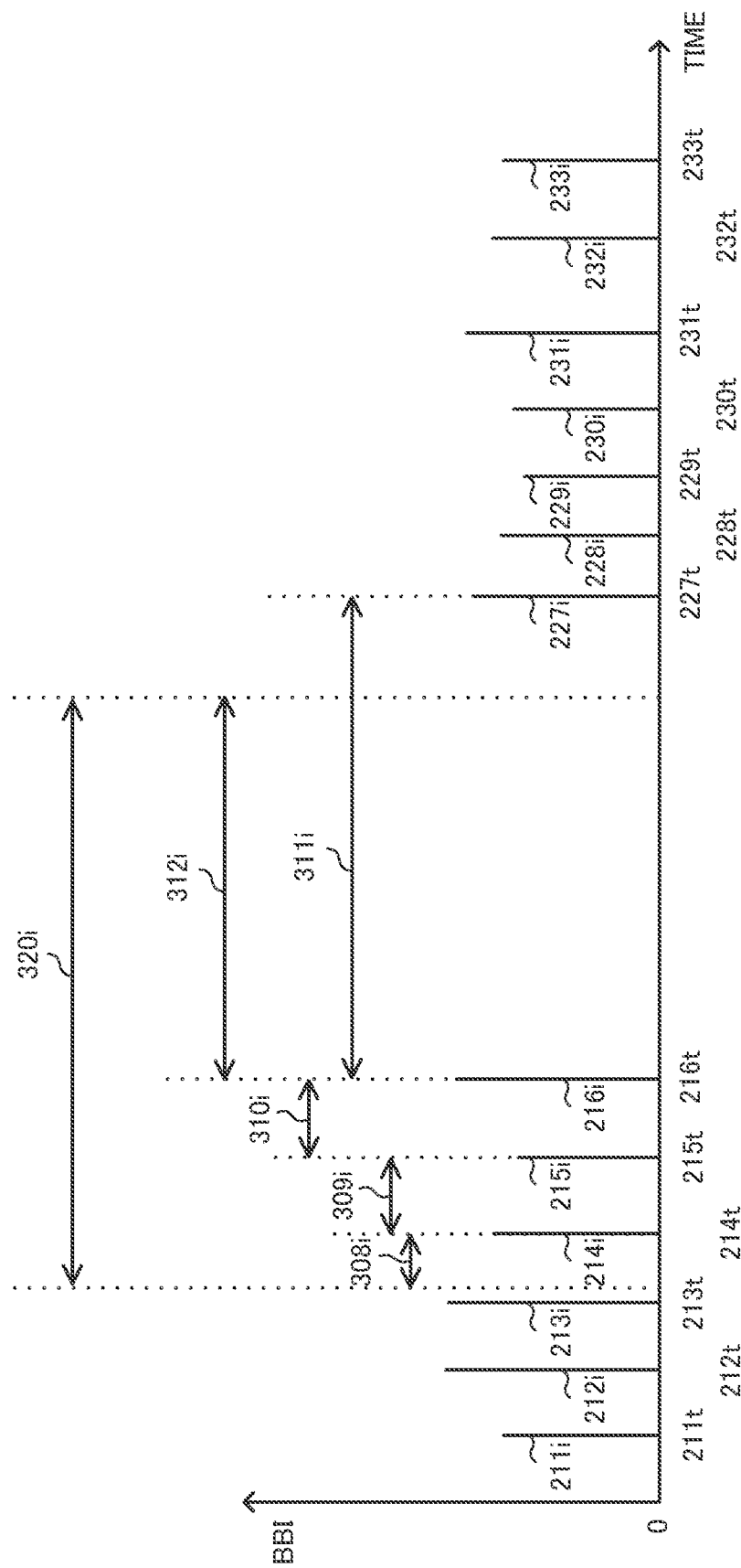
FIG. 13 is a diagram for explaining a BBI non-acquisition period.

According to Embodiment 1, a BBI correction procedure is determined among the first and second correction procedures based on the comparison between the outlier ratios calculated by the outlier ratio calculator 12 and the outlier ratio threshold. The outlier ratios are only an example of the value used in this determination. For example, the determination may be based on the time length of the longest BBI non-acquisition period encompassed in a certain period including the focused timing (for example, the three seconds having the focused timing at the center). The BBI non-acquisition period indicates a period in which no BBI is acquired from the data array of BBIs after removal of BBI outliers. Examples of BBI non-acquisition period include periods 309i, 310i, and 311i as illustrated in FIG. 13. The BBI non-acquisition period that is longest among the BBI non-acquisition periods encompassed in the certain period is called a longest non-acquisition period. For example, in the case where the certain period is a period 320i in FIG. 13, the period 320i encompasses BBI non-acquisition periods including periods 308i, 309i, 310i, and 312i, among which the period 312i is longest and regarded as the longest non-acquisition period. The following description focuses on Embodiment 2 involving the determination based on the time length of the longest non-acquisition period.

Figure 14:
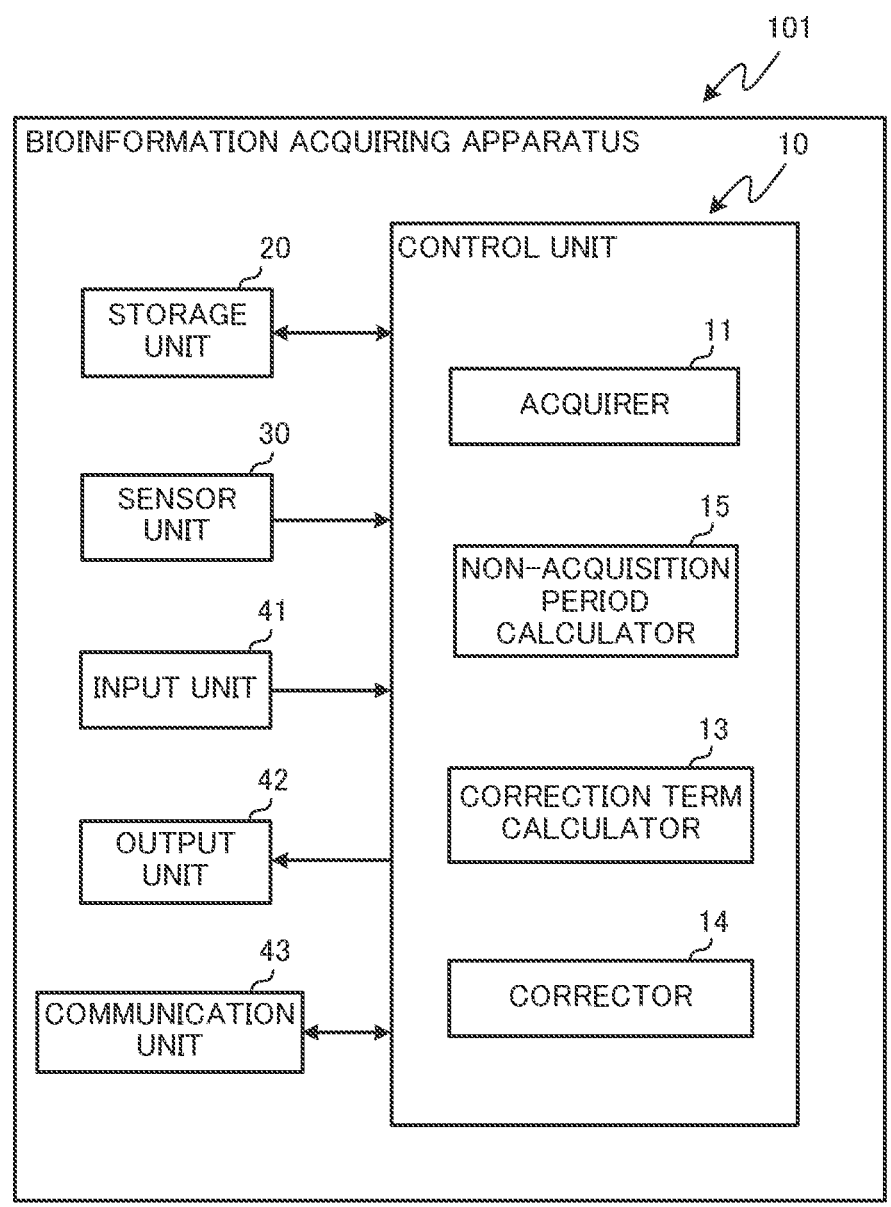
FIG. 14 illustrates an exemplary configuration of a bioinformation acquiring apparatus according to Embodiment 2.

With reference to FIG. 14, the functional configuration of a bioinformation acquiring apparatus 101 according to Embodiment 2 is configured by replacing the outlier ratio calculator 12 with a non-acquisition period calculator 15 in the bioinformation acquiring apparatus 100 according to Embodiment 1.

The non-acquisition period calculator 15 calculates, as outlier level parameters, the longest non-acquisition periods from the data array of BBIs after removal of BBI outliers from the BBIs (data array of BBIs) acquired by the acquirer 11 within the first duration (for example, one minute).

The non-acquisition period calculator 15 may calculate longest outlier occurrence periods as outlier level parameters, instead of the longest non-acquisition periods. The longest outlier occurrence period indicates an outlier occurrence period that is longest among the outlier occurrence periods encompassed in the certain period (for example, the three seconds having the focused timing at the center) including the focused timing. The outlier occurrence period indicates a period between two BBIs (not outliers) adjacent to each other in which at least one BBI outlier occurs. A typical example of outlier occurrence period is the period 311i illustrated in FIG. 6.

In the calculation of non-acquisition periods in this embodiment, the non-acquisition period calculator 15 calculates BBI non-acquisition periods in which no BBI is acquired based on the data array of BBIs after removal of BBI outliers from all the BBIs acquired within the first duration including the focused timing (for example, the one minute having the focused timing at the center), while shifting the focused timing along the time axis. The non-acquisition period calculator 15 then calculates the longest non-acquisition period, which is a non-acquisition period longest among the calculated BBI non-acquisition periods.

The non-acquisition period calculator 15 calculates such longest non-acquisition periods while shifting the focused timing, and thereby provides a single longest non-acquisition period every focused timing. The time displacement (calculation cycle of longest non-acquisition periods (outlier level parameters)) of shifting of the focused timing may be any value. In this embodiment, the time displacement is also defined to be one second identical to the cycle of resampling interpolation in BBIs, for the same reason as in Embodiment 1. That is, the non-acquisition period calculator 15 calculates a longest non-acquisition period every one second.

If the longest non-acquisition period calculated by the non-acquisition period calculator 15 is at least a certain threshold (duration threshold THT (for example, ten seconds)), the corrector 14 corrects the BBI outliers within the first duration by the first correction procedure using the correction terms calculated by the correction term calculator 13. In contrast, if the longest non-acquisition period calculated by the non-acquisition period calculator 15 is shorter than the certain threshold (duration threshold THT), the corrector 14 corrects the BBI outliers by the second correction procedure involving interpolation irrelevant to the correction terms calculated by the correction term calculator 13. The second correction procedure is explained above. The duration threshold THT may be determined depending on the time length of the first duration (for example, the tenth of the first duration).

The above description is directed to the differences in the functional configuration of the bioinformation acquiring apparatus 101 from those of the bioinformation acquiring apparatus 100. The following explanation focuses on individual operations executed by the control unit 10 of the bioinformation acquiring apparatus 101 according to Embodiment 2.

Figure 11:
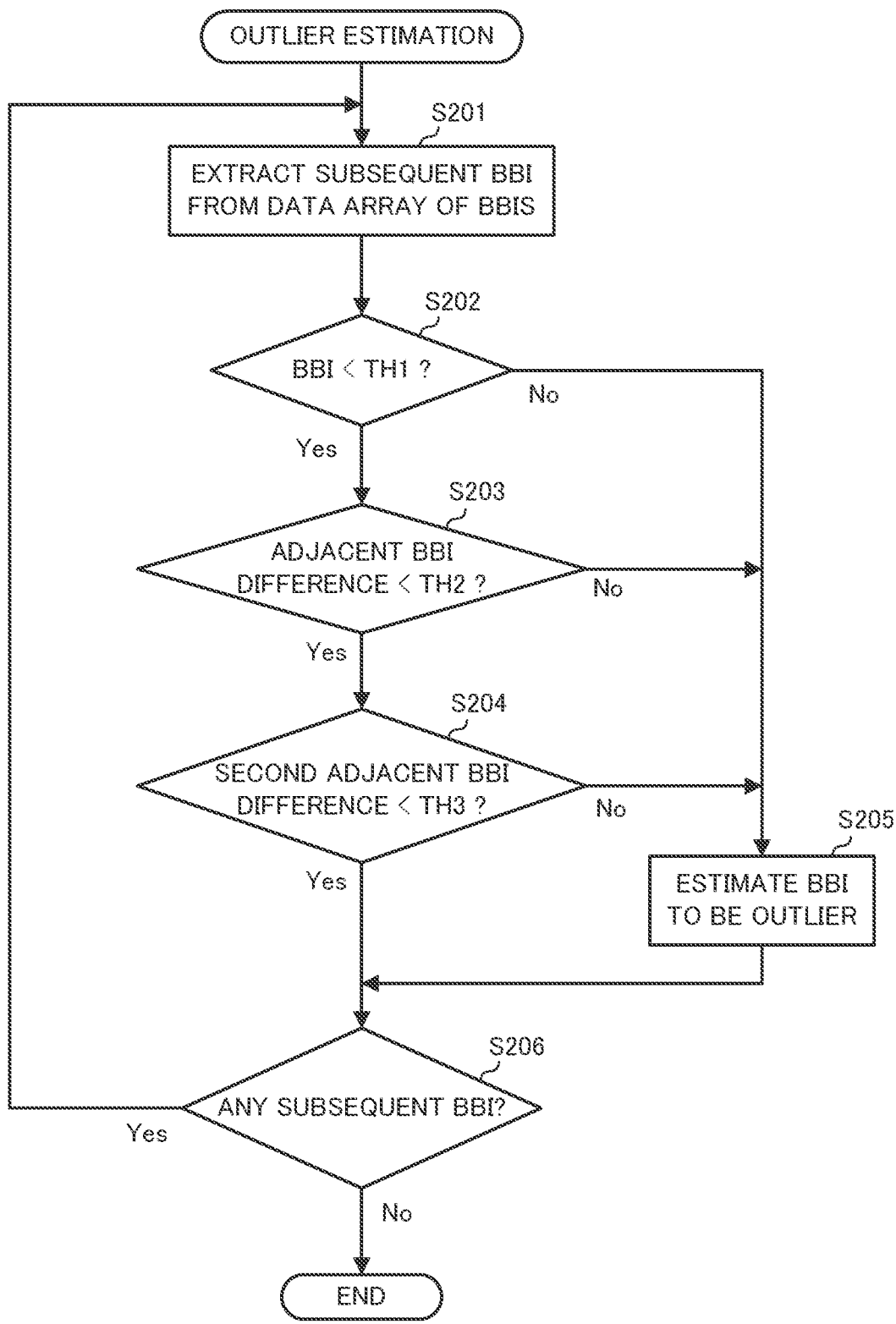
FIG. 11 is a flowchart of an outlier estimation according to Embodiment 1.

The outlier estimation according to Embodiment 2 is identical to the outlier estimation according to Embodiment 1, as illustrated in FIG. 11. It should be noted that the outlier estimation is executed by not the outlier ratio calculator 12 but the non-acquisition period calculator 15.

The bioinformation acquiring process and the BBI correction in the bioinformation acquiring apparatus 101 according to Embodiment 2 differ from the bioinformation acquiring process and the BBI correction in the bioinformation acquiring apparatus 100 according to Embodiment 1 in some respects. These differences will now be explained in sequence.

Figure 9:
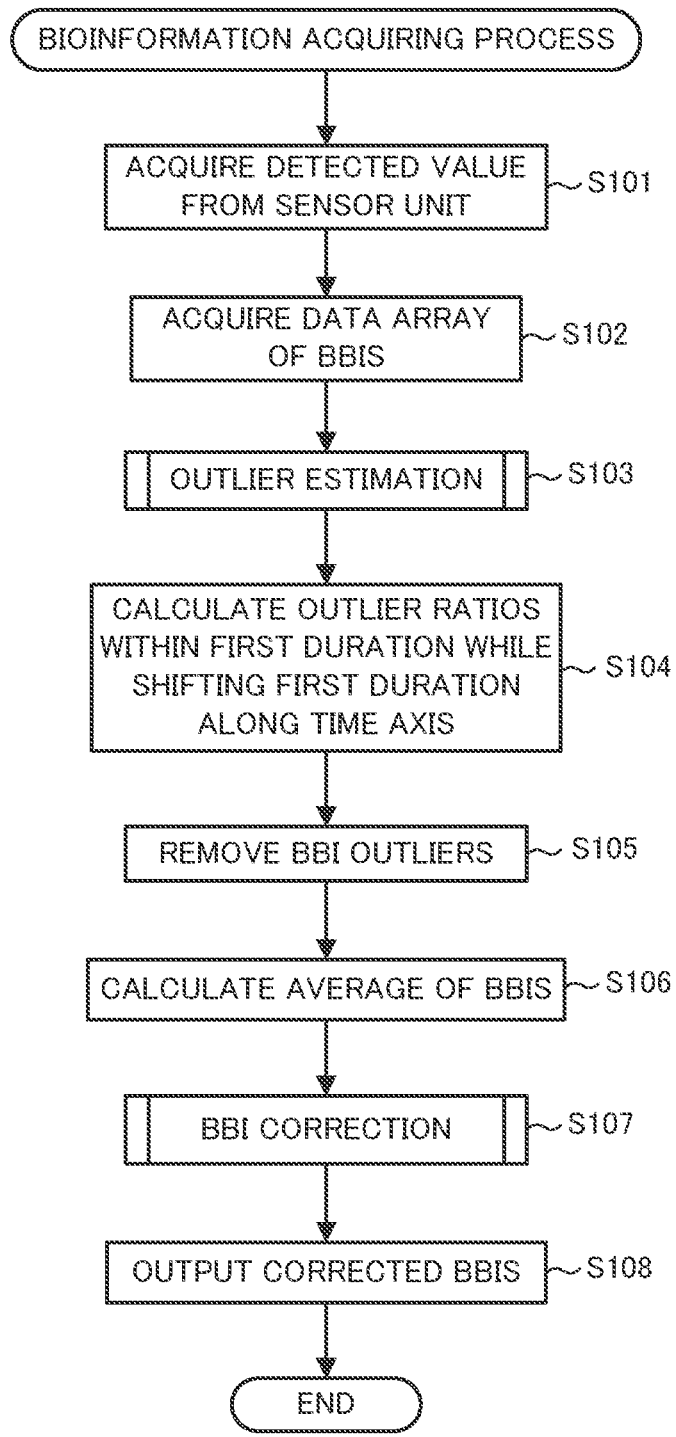
FIG. 9 is a flowchart of a bioinformation acquiring process according to Embodiment 1.
Figure 15:
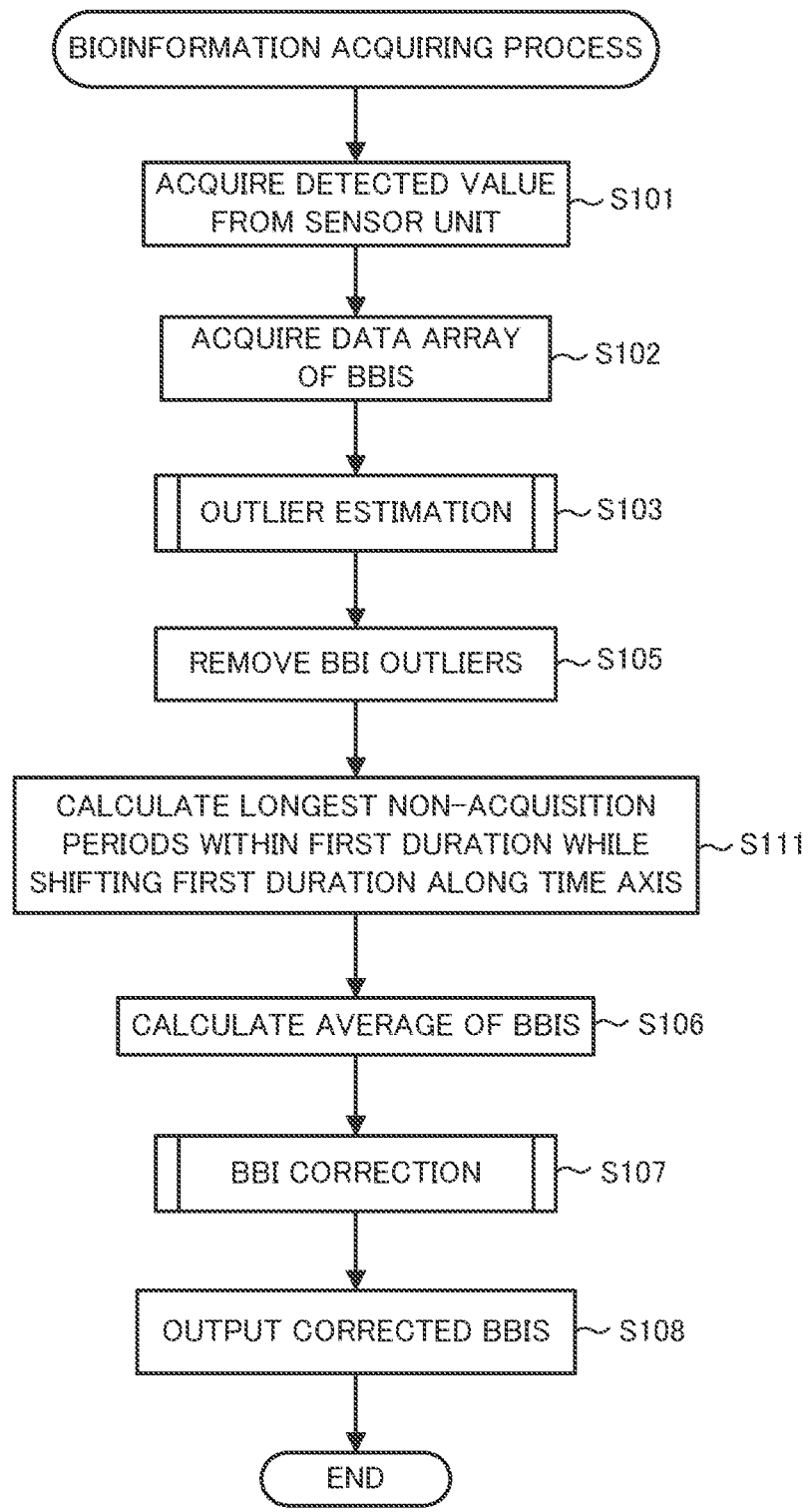
FIG. 15 is a flowchart of a bioinformation acquiring process according to Embodiment 2.

The bioinformation acquiring process in the bioinformation acquiring apparatus 101 according to Embodiment 2 is configured by deleting Step S104 from the bioinformation acquiring process (FIG. 9) in the bioinformation acquiring apparatus 100 according to Embodiment 1 and adding Step S111 between Steps S105 and S106, as illustrated in FIG. 15. The non-acquisition period calculator 15 executes the steps executed by the outlier ratio calculator 12 in the bioinformation acquiring process in the bioinformation acquiring apparatus 100 according to Embodiment 1. The bioinformation acquiring process in the bioinformation acquiring apparatus 101 according to Embodiment 2 will now be explained with reference to FIG. 15, focusing on the differences from Embodiment 1 (FIG. 9).

Steps S101 to S105 are identical to the steps of the bioinformation acquiring process according to Embodiment 1, except for the absence of Step S104.

In Step S111, the non-acquisition period calculator 15 calculates longest non-acquisition periods (data array of longest non-acquisition periods in the chronological order) from the data array of BBIs within the first duration including the focused timing, while shifting the focused timing along the time axis by a certain time (for example, one second). The non-acquisition period calculator 15 then stores all the calculated longest non-acquisition periods into the storage unit 20.

Steps S106 and S108 are identical to those of the bioinformation acquiring process according to Embodiment 1. The BBI correction in Step S107, however, differs from the BBI correction according to Embodiment 1.

Figure 16:
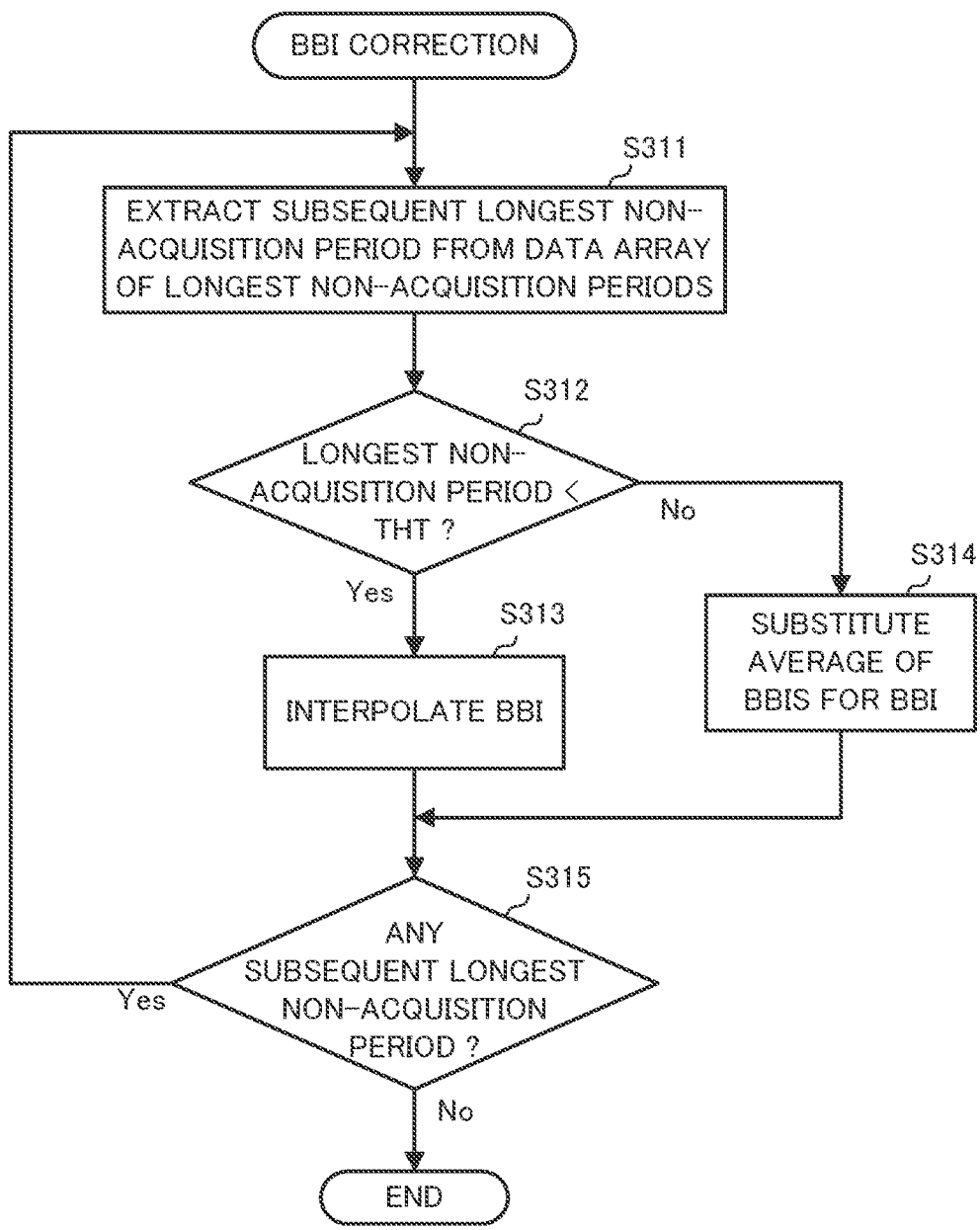
FIG. 16 is a flowchart of a BBI correction according to Embodiment 2.

The BBI correction in the bioinformation acquiring apparatus 101 according to Embodiment 2 will now be explained with reference to FIG. 16. This process involves resampling interpolation in BBIs at a resampling frequency (for example, 1 Hz), as in Embodiment 1. In this embodiment, since the resampling frequency is adjusted to 1 Hz in accordance with the one second as the calculation cycle of longest non-acquisition periods, a single BBI should be resampled every time when a single longest non-acquisition period is extracted, as in Embodiment 1. The data array of longest non-acquisition periods is also on the same time axis as the data array of BBIs and the data array of correction terms. Accordingly, in the following explanation, the longest non-acquisition period, the BBI, and the correction term at a certain focused timing (t) are respectively represented by P[t], B[t], and C[t]. Also, the data at the timing immediately after the focused timing (t) on the time axis are respectively represented by P[t+1], B[t+1], and C[t+1].

The corrector 14, first, sequentially reads a longest non-acquisition period as a focused longest non-acquisition period (P[t]) from the data array of longest non-acquisition periods in the chronological order stored in the storage unit 20 in the order of storage of longest non-acquisition periods (Step S311). The corrector 14 then determines whether the focused longest non-acquisition period (P[t]) is shorter than the duration threshold THT (for example, ten seconds), which is shorter than the first duration (Step S312).

If the focused longest non-acquisition period is shorter than the duration threshold THT (Step S312; Yes), the corrector 14 resamples the BBI (B[t]) associated with the focused timing associated with the focused longest non-acquisition period (P[t]) by an interpolation procedure of substituting an BBI after outlier removal for the BBI (B[t]) (Step S313). This step may involve any interpolation procedure. Exemplary interpolation procedures include spline interpolation, as described above.

In contrast, if the focused longest non-acquisition period (P[t]) is not shorter than the duration threshold THT (Step S312; No), the corrector 14 resamples the BBI (B[t]) associated with the focused timing associated with the focused longest non-acquisition period (P[t]) by substituting the correction term associated with the focused timing (that is, the correction term (C[t]) calculated by the correction term calculator 13) for the BBI (B[t]) (Step S314). Alternatively, in Steps S313 and S314, the corrector 14 may correct (resample) only outliers while maintaining the BBIs except for the outliers as they are, as a BBI associated with each focused timing, as in Steps S303 and S304.

The corrector 14 then determines whether the data array of longest non-acquisition periods stored in the storage unit 20 contains any longest non-acquisition period (P[t+1]) subsequent to the focused longest non-acquisition period (P[t]) (Step S315). If the data array contains any subsequent longest non-acquisition period (Step S315; Yes), the processing returns to Step S311 (in Step S311, (t) is incremented to (t+1)). If the data array contains no subsequent longest non-acquisition period (Step S315; No), the corrector 14 terminates the BBI correction, and then the processing returns to Step S108 of the bioinformation acquiring process.

The above-explained bioinformation acquiring process, outlier estimation, and BBI correction can achieve appropriate selection of a correction (resampling) procedure for BBIs depending on the longest non-acquisition periods. This configuration is capable of appropriate correction of BBIs, as in Embodiment 1, even in the case where outliers cannot be appropriately removed (for example, a BBI cannot be acquired for a long time, or a large number of BBIs are removed as outliers).

Modification

In the BBI correction (FIG. 12 or 16) according to the above-described embodiments, a correction (resampling) procedure is selected based on the comparison between the outlier level parameters and the threshold. In this configuration, the corrected BBIs are discontinuous in some cases at the timings of switching of correction procedures (for example, timings 214t and 229t in FIG. 8).

For the timings of switching of correction procedures, the corrector 14 may correct the BBIs into the average of the values provided by the individual correction procedures. In this case, the corrector 14 preliminarily stores the previously selected correction procedure in order to determine whether the focused timing is a timing of switching of correction procedures. If the currently selected correction procedure differs from the previously selected correction procedure, the corrector 14 determines that the focused timing is a timing of switching of correction procedures. If determining that the focused timing is a timing of switching of correction procedures, the corrector 14 corrects the BBI (B[t]) associated with the focused timing into the average of the value (correction term (C[t])) provided by the first correction procedure and the value (interpolation value in BBIs) provided by the second correction procedure. In this case, the corrector 14 selects both of the first and second correction procedures.

Alternatively, the corrector 14 may correct each BBI into the average of the values provided by the individual correction procedures not only at the timings of switching of correction procedures but also in a certain period including each of these timings (for example, ten seconds before and after the timings). In this case, the corrector 14 preliminarily stores a history of selected correction procedures for the previous certain period, in order to determine whether the focused timing is within the certain period including a timing of switching of correction procedures. If the history of correction procedures contains the first and second correction procedures, the corrector 14 determines that the focused timing is within the certain period including a timing of switching of correction procedures. If determining that the focused timing is within the certain period including a timing of switching of correction procedures, the corrector 14 corrects the BBI (B[t]) associated with the focused timing into the average of the value (correction term (C[t])) provided by the first correction procedure and the value (interpolation value in BBIs) provided by the second correction procedure.

Figure 17:
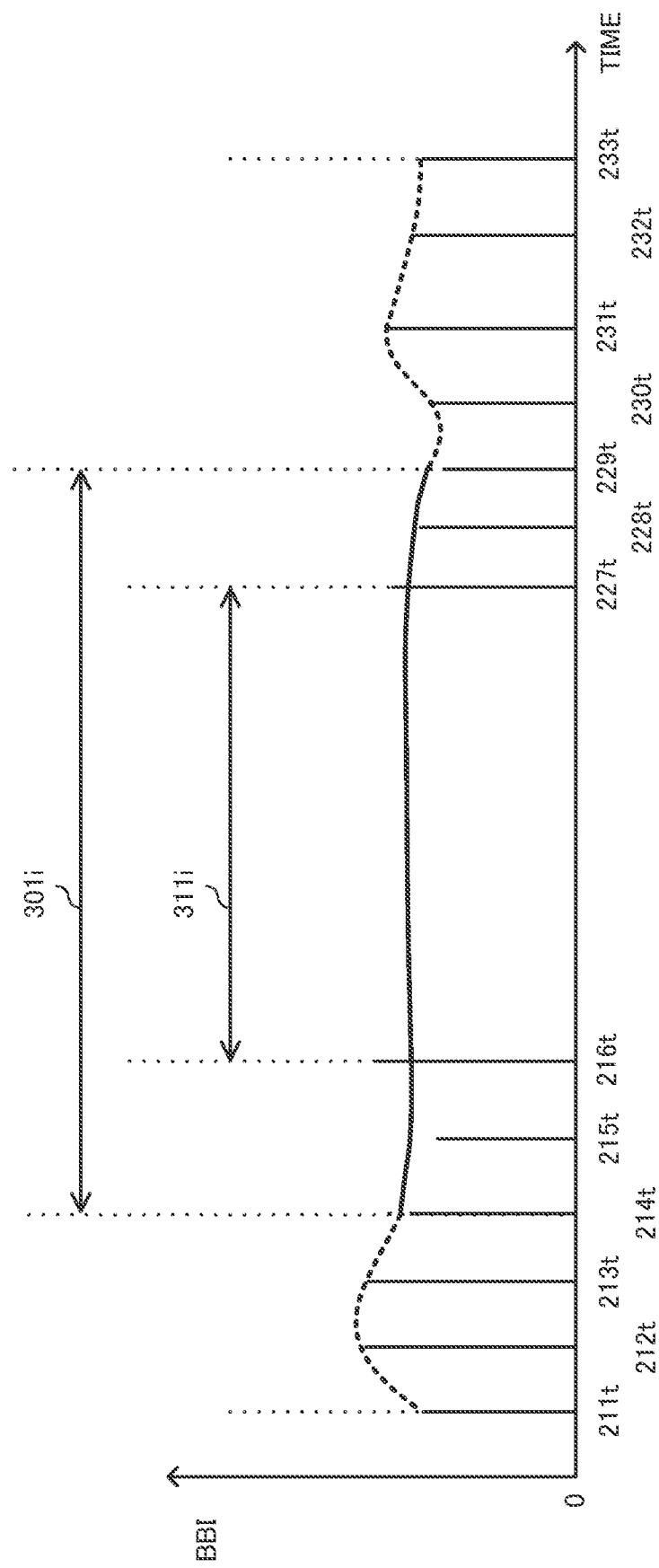
FIG. 17 illustrates an example in which BBIs are corrected so as not to be discontinuous at the timings of switching correction procedures between correction using correction terms and spline interpolation.

This process can correct, for example, the discontinuous BBIs as illustrated in FIG. 8 into the continuous BBIs as illustrated in FIG. 17, thereby achieving more appropriate correction of heartbeat intervals. In this modification, the corrector 14 may also correct a BBI into a value other than the simple average of the value provided by the first correction procedure and the value provided by the second correction procedure. For example, the corrector 14 may correct a BBI into a weighted average of the value provided by the first correction procedure and the value provided by the second correction procedure, for example, depending on the ratio between the first and second correction procedures included in the history of correction procedures.

Other Modifications

According to the above-described embodiments, the sensor detects a value for acquiring heartbeat intervals as bioinformation, and the corrector 14 acquires uniform RRIs through resampling based on the acquired heartbeat intervals. Alternatively, the corrector 14 may correct only outliers through resampling. In this configuration, the corrector 14 acquires uniform RRIs only during a period including any outlier, and acquires raw data on heartbeat intervals during the other periods. The bioinformation may also be information other than heartbeat intervals. The bioinformation acquiring apparatus 100 or 101 can also perform appropriate correction of any bioinformation other than heartbeat intervals, provided that the bioinformation is subject to outlier removal and is then corrected through resampling interpolation or the like.

In the case where the bioinformation acquiring apparatus 100 or 101 is capable of receiving bioinformation or a detected value for acquiring bioinformation via the communication unit 43 from an external device, for example, the bioinformation acquiring apparatus 100 or 101 may exclude the sensor unit 30.

According to the above-described embodiments, the correction term for heartbeat intervals is the average (moving average) of BBIs after removal of BBI outliers from the BBIs acquired within the time window having the second duration including the focused timing. The correction term, however, should not necessarily be the average. The correction term calculator 13 may also calculate, as a correction term, the mean (moving mean) or mode (moving mode) of BBIs after removal of BBI outliers from the BBIs acquired within the time window having the second duration including the focused timing. Alternatively, the correction term calculator 13 may calculate, as a correction term, the average, mean, or mode of all the BBIs after removal of BBI outliers from the BBIs within a duration, for example, from when the human subject goes to bed until when the human subject gets up, instead of the second duration including the focused timing.

According to the above-described embodiments, the ballistocardiogram signals for one night, that is, from when the human subject goes to bed until when the human subject gets up, are acquired in Step S101 of the bioinformation acquiring process (FIG. 9 or 15). The data for one night, however, should not necessarily be acquired. The processing may go to Step S102 after acquisition of data for a certain period (for example, one hour), followed by the above-explained operations using the data (for example, data for one hour) that is acquired thus far, go to Step S108, and then return to Step S101, so as to repeat the bioinformation acquiring process every certain period.

According to the above-described embodiments, the calculation of an outlier level parameter and the BBI correction are performed every one second. The cycles of these steps, however, should not necessarily be one second. For example, these steps may also be executed at once every first duration. In addition, the outlier level parameters are calculated while the first duration is being shifted along the time axis according to the above-described embodiments. Alternatively, the outlier level parameters may be calculated within the first duration fixed on the time axis, followed by correction of outliers of bioinformation within the first duration.

According to the above-described embodiments, the bioinformation acquiring apparatus 100 or 101 includes the input unit 41, the output unit 42, and the communication unit 43. These components, however, are not essential components and may be excluded from the bioinformation acquiring apparatus 100 or 101.

According to one of the above-described embodiments, the outlier level parameter is an outlier ratio indicating the ratio of inclusion of outlier. The outlier level parameter, however, should not necessarily be an outlier ratio. For example, the outlier level parameter may also be the inverse of the outlier ratio or the number of occurrence of outliers. The outlier ratio calculator 12 may derive outlier level parameters by using a table or the like instead of calculating (deriving) the outlier level parameters by using an expression or the like.

According to the above-described embodiments, the bioinformation acquiring apparatus 100 or 101 acquires heartbeat intervals of a human subject. Alternatively, the acquisition target may be a general animal, such as dog, cat, horse, cow, pig, or chicken, other than a human. For such an animal subject, the bioinformation acquiring apparatus 100 or 101 can also perform appropriate correction of bioinformation depending on outlier level parameters.

The individual functions of the bioinformation acquiring apparatus 100 or 101 can also be achieved by a computer, such as a general personal computer (PC). Specifically, in the above-described embodiments, the programs for the processes, such as the bioinformation acquiring process, executed by the bioinformation acquiring apparatus 100 or 101 are preliminarily stored in the ROM of the storage unit 20. Alternatively, these programs may be stored in a non-transitory computer-readable recording medium, such as a flexible disk, a compact disc read only memory (CD-ROM), a digital versatile disc (DVD), a magneto-optical disc (MO), a memory card, or a universal serial bus (USB) memory to be distributed. These programs on the recording medium may be read and installed in the computer, so that the computer can achieve the functions of the bioinformation acquiring apparatus 100 or 101.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

What is claimed is:

1. A bioinformation acquiring apparatus comprising:
   at least one processor configured to:
   acquire heartbeat intervals, as bioinformation, in a chronological order from a ballistocardiogram waveform, wherein the heartbeat intervals do not have a uniform time length because of fluctuations in heartbeats;
   derive outlier ratios, each of the outlier ratios indicating a level of inclusion of outliers of the bioinformation in pieces of the bioinformation acquired within a first duration including a focused timing, while shifting the focused timing along a time axis;
   derive correction terms, each of the correction terms being a representative value of the bioinformation after removal of the outliers of the bioinformation from pieces of the bioinformation acquired within a second duration, that is longer than the first duration and encompasses the first duration, including the focused timing while shifting the focused timing along the time axis;
   correct, using the correction terms, the outliers in the heartbeat intervals using the correction terms within a period in which the outlier ratios are at least a threshold, according to a first correction procedure;
   correct the outliers in the heartbeat intervals by a second correction procedure involving interpolation irrelevant to the correction terms where the outlier ratios are lower than the threshold; and
   output a corrected heartbeat as a result of correction of the heartbeat intervals by the first correction procedure and the second correction procedure.

2. The bioinformation acquiring apparatus according to claim 1,
   wherein the at least one processor is configured to:
   calculate non-acquisition periods in which no bioinformation is acquired, based on the bioinformation after removal of the outliers of the bioinformation from the pieces of the bioinformation acquired within the first duration; and
   calculate longest non-acquisition periods as the outlier ratios, the longest non-acquisition periods each indicating a period that is longest among the calculated non-acquisition periods.

3. The bioinformation acquiring apparatus according to claim 1,
   wherein the at least one processor is configured to derive, as the correction terms, moving averages obtained by calculating averages of the pieces of the bioinformation after removal of the outliers of the bioinformation from the pieces of the bioinformation acquired within the second duration while shifting the second duration along the time axis.

4. The bioinformation acquiring apparatus according to claim 1,
   wherein the at least one processor is configured to:
   determine whether a focused timing is a timing of switching of the correction procedures to be selected;
   in response to determining that the focused timing is the timing of switching of the correction procedures, select, as the correction procedure, both of the first correction procedure using the correction terms and the second correction procedure involving interpolation irrelevant to the correction terms; and
   in response to determining that both of the first correction procedure and the second correction procedure are selected as the correction procedure, correct each of the outliers of the bioinformation within the first duration using an average of a value provided by the first correction procedure and a value provided by the second correction procedure.

5. The bioinformation acquiring apparatus according to claim 1,
   wherein the at least one processor is configured to determine each of the heartbeat intervals to be an outlier, if the heartbeat interval is at least a first threshold, if an adjacent interval difference is at least a second threshold, or if a second adjacent interval difference is at least a third threshold, where the adjacent interval difference indicating an absolute value of a difference between adjacent heartbeat intervals, the second adjacent interval difference indicating a sum of the adjacent interval difference and another adjacent interval difference adjacent thereto.

6. A bioinformation acquiring method comprising:
   acquiring heartbeat intervals, as bioinformation, in a chronological order from a ballistocardiogram waveform, wherein the heartbeat intervals do not have a uniform time length because of fluctuations in heartbeats;
   deriving outlier ratios, each of the outlier ratios indicating a level of inclusion of outliers of the bioinformation in pieces of the bioinformation acquired within a first duration including a focused timing, while shifting the focused timing along a time axis;
   deriving correction terms, each of the correction terms being a representative value of the bioinformation after removal of the outliers of the bioinformation from pieces of the bioinformation acquired within a second duration that is longer than the first duration and encompasses the first duration, including the focused timing while shifting the focused timing along the time axis;
   correcting, using the correction terms, the outliers in the heartbeat intervals using the correction terms within a period in which the outlier ratios are at least a threshold, according to a first correction procedure;

correcting the outliers in the heartbeat intervals by a second correction procedure involving interpolation irrelevant to the correction terms where the outlier ratios are lower than the threshold; and outputting a corrected heartbeat as a result of correction of the heartbeat intervals by the first correction procedure and the second correction procedure.

7. A non-transitory recording medium storing a program causing a computer to execute:

acquiring heartbeat intervals, as bioinformation, in a chronological order from a ballistocardiogram waveform, wherein the heartbeat intervals do not have a uniform time length because of fluctuations in heartbeats;

deriving outlier ratios, each of the outlier ratios indicating a level of inclusion of outliers of the bioinformation in pieces of the bioinformation acquired within a first duration including a focused timing, while shifting the focused timing along a time axis;

deriving correction terms, each of the correction terms being a representative value of the bioinformation after removal of the outliers of the bioinformation from pieces of the bioinformation acquired within a second duration that is longer than the first duration and encompasses the first duration, including the focused timing while shifting the focused timing along the time axis;

correcting, using the correction terms, the outliers in the heartbeat intervals using the correction terms within a period in which the outlier ratios are at least a threshold, according to a first correction procedure;

correcting the outliers in the heartbeat intervals by a second correction procedure involving interpolation irrelevant to the correction terms where the outlier ratios are lower than the threshold; and outputting a corrected heartbeat as a result of correction of the heartbeat intervals by the first correction procedure and the second correction procedure.

\* \* \* \* \*